United States Patent
Hao et al.

(10) Patent No.: US 11,041,856 B2
(45) Date of Patent: *Jun. 22, 2021

(54) USE OF FLUORESCENCE FOR THE QUICK AND EASY DETERMINATION OF S-ADENOSYLMETHIONINE, S-ADENOSYLHOMOCYSTEINE AND HOMOCYSTEINE

(71) Applicants: Xiujuan Hao, Chantilly, VA (US); Chaoyi Deng, Changsha (CN)

(72) Inventors: Xiujuan Hao, Chantilly, VA (US); Chaoyi Deng, Changsha (CN)

(73) Assignee: HUNAN SKYWORLD BIOTECHNOLOGIES CO, Changsha (CN)

( * ) Notice: Subject to any disclaimer, the term of this patent is extended or adjusted under 35 U.S.C. 154(b) by 128 days.

This patent is subject to a terminal disclaimer.

(21) Appl. No.: 16/120,418

(22) Filed: Sep. 3, 2018

(65) Prior Publication Data
US 2018/0372735 A1 Dec. 27, 2018

Related U.S. Application Data

(63) Continuation of application No. 15/164,856, filed on May 25, 2016, now Pat. No. 10,067,126.

(60) Provisional application No. 62/166,044, filed on May 25, 2015.

(51) Int. Cl.
| *G01N 33/543* | (2006.01) |
| *G01N 33/533* | (2006.01) |
| *A61K 49/00* | (2006.01) |
| *C07K 16/44* | (2006.01) |

(52) U.S. Cl.
CPC ..... *G01N 33/54373* (2013.01); *G01N 33/533* (2013.01); *A61K 49/0058* (2013.01); *C07K 16/44* (2013.01); *G01N 2333/4737* (2013.01); *G01N 2800/50* (2013.01)

(58) Field of Classification Search
CPC ..... G01N 33/54373; G01N 2333/4737; G01N 2800/52; G01N 33/15; G01N 33/532; G01N 33/533; C09K 11/00; C09K 11/06; C09K 16/44; A61K 49/0058
See application file for complete search history.

(56) References Cited

U.S. PATENT DOCUMENTS

2013/0172361 A1* 7/2013 Fava ............... C12Q 1/6883
514/250
2019/0339283 A1* 11/2019 Hao ............... C07J 43/003

OTHER PUBLICATIONS

Bunzil, Jean-Claude. Lanthanide luminescence for biomedical analyses and imaging. Chem. Rev. 2010, vol. 110, pp. 2729-2755. (Year: 2010).*

* cited by examiner

*Primary Examiner* — Shafiqul Haq
(74) *Attorney, Agent, or Firm* — Isaac Angres

(57) ABSTRACT

The invention provides immunochromatographic test strips and methods and systems or kits for detecting and quantifying S-Adenosylmethionine (SAM), S-Adenosylhomocysteine (SAH) and Homocysteine (HCy) in a sample, comprising: (a) making fluorophore conjugated antibodies; (b) immobilizing SAM, SAH and HCy on a solid support; (c) providing a sample, combining said sample with a conjugate selected from the group consisting of lanthanide chelate conjugates and quantum dot conjugates (QD) with anti-SAM, anti-SAH or anti-HCy, wherein said combining is performed under conditions that allow formation of a competitive complex comprising said conjugate, said SAM, SAH or HCy on the solid support and SAM, SAH or HCy in a sample when present; and (d) detecting the presence of the complex, if present, by monitoring a spectral emission mediated by the fluorescent conjugates in the complex, wherein the emission indicates the presence and quantity of SAM, SAH or HCy in the sample.

2 Claims, 7 Drawing Sheets

A

B

Concentration of C-Reaction Protein (mg/L)

A

B

C

D

A

B

USE OF FLUORESCENCE FOR THE QUICK AND EASY DETERMINATION OF S-ADENOSYLMETHIONINE, S-ADENOSYLHOMOCYSTEINE AND HOMOCYSTEINE

This application is a continuation of pending U.S. patent application Ser. No. 15/164,856 filed May 25, 2016; the entire contents of which are incorporated by reference herein. This application also claims the priority benefit under 35 U.S.C. section 119 of U.S. provisional Patent Application No. 62/166,044 entitled "Use Of Immunological And Chemical Methods For The Quick And Easy Determination Of SAM, S-Adenosylhomocysteine And Homocysteine" filed on May 25, 2015, and which is in its entirety herein incorporated by reference.

FIELD OF THE INVENTION

The present invention relates to the use of fluorescent materials such as quantum dots, fluorescent lanthanide metal chelate complexes, and colloidal microspheres in the immunological determination of S-adenosylmethionine (SAM), S-adenosylhomocysteine (SAH), and C-reaction protein (CRP). The invention further relates to the use of a photochemical method for the determination of homocysteine (HCy) in a dry strip and the combinations of both methods. The invention further relates to the quantitative measurement of SAM, SAH and HCy simultaneously using fluorescence-optical density devices that read immunological fluorescence and photochemical colors simultaneously for quick and convenient reporting. The present invention further relates to assays of clinical samples.

This invention also relates to fluorescent compounds useful as indicator molecules for detecting the presence or concentration of an analyte in a medium, such as a liquid, and to methods for achieving such detection. More particularly, the invention relates to fluorescent lanthanide metal chelate complexes and their use as indicator molecules for detecting the presence or concentration of an analyte such as SAM, SAH and CRP in a medium, including a liquid medium such as a biological fluid or other biological samples.

The invention additionally relates to the development of an assay system capable of discriminating mixtures of cardiovascular risk factor analytes for the prediction of coronary heart disease and stroke. The invention is also directed to the determination of SAM and SAH, HCy and CRP to determine cardiac care and cardiac prognosis. The instant invention is also particularly useful in the field of in vitro diagnosis (IVD) and point-of-care testing (POCT).

BACKGROUND OF THE INVENTION

In biology it is of interest to mark structures such as cells or viruses with fluorescent materials for accurate identification, ease of detection and microscopic analysis. Traditionally, organic dye fluorophores have been the favored materials and have the capability to be modified with a range of materials, enabling targeted binding to a wide range of biological structures based on known affinities and chemistries. Upon binding of the dye to the target biological material, an activating light of a given wavelength is used to excite the dye, from which it responds by fluorescently emitting a characteristic light radiation specific to the properties of the organic dye employed. However, traditional organic dyes have numerous limitations when used to tag biological materials.

Semiconductor fluorescent nanocrystals ("quantum dots") are nanometer sized semiconductor, light-emitting crystals, spherical in shape and have superior fluorescent properties to organic dyes. Quantum dots are generally synthesized with Type II-VI (e.g. CdSe, CdTe, CdS and ZnSe) or Type III-V (e.g. InP and InAs) column elements from the periodic table and can be capped with numerous shells, layers or molecules to modify their physical properties, such as for surface functionalization. Integration of quantum dots in biology was achieved in breakthroughs showing that highly luminescent quantum dots could be made water-soluble and subsequently biocompatible using surface modification techniques such as silica/siloxane coatings or direct absorption of bifunctional ligands, which presented them useful tools in biology. Quantum dots are emerging as the new biological label with applications and properties superior to traditional fluorescent proteins and organic dyes.

Most of the limitations with traditional organic dyes are a result of the extremely limited absorptive and emissive capabilities. The first shortcoming is that the peak emission of organic dyes cannot be altered—each dye corresponds to a different molecule with a different pre-set emission wavelength, or fluorescent color, that is set by nature. The second shortcoming is the narrow absorption pattern of organic dyes—dyes tend to display absorption peaks that are not always in convenient regions of the spectrum, making the excitation of various organic dyes challenging and costly. The third shortcoming is that of uneven absorption and emission peaks—organic dyes have a tendency to produce "shoulders" in the geometry of their emission and absorption peaks, which is a major disadvantage in applications that require Gaussian type emission patterns to work correctly. An additional shortcoming is that of stability—the lifetime of organic dyes varies but is generally low relative to that of other tagging mechanisms and organic dye fluorescence is controlled entirely by the molecular bonding properties of each individual dye. Finally, incident radiation absorbed by an organic dye molecule moves electrons into excited states, whereupon they decay and release light radiation. This emission cannot be altered because it corresponds to pre-set excited states of the dye molecule that are inherent to every molecule of that type.

Whereas the light emission ranges and possible forms of organic dyes are very limited, quantum dots can be made to emit light at any wavelength in the visible and infrared ranges, and can be inserted almost anywhere, including in liquid solutions, dyes, paints, epoxies, and sol-gels. Furthermore, quantum dots can be attached to a variety of surface ligands, and inserted into a variety of organisms in vivo or in vitro.

Numerous methods exist for covalently linking biological molecules to quantum dots to create a bio-molecular conjugates ("bioconjugate") or functional quantum dot which are used in labeling, detection and imaging applications to attach or bind a quantum dot to a biological material based on specific chemical or biological affinity. These methods employ a variety of chemistries to water-soluble quantum dots from which several cross-linker molecules can be coupled to enable the attachment of the primary functional biomaterial. Other examples of bioconjugate techniques enabling the attachment of various materials to quantum dots are known to those skilled in the art.

Generally, bioconjugation methods are classified into mechanisms using: (1) Biofunctional linkages, (2) Electrostatic attraction, (3) Hydrophobic attraction, (4) Silanization, and (5) Nanobead linkages. Examples of methods employing bioconjugative techniques are polyethylglycol modification of the underlying carboxyl quantum dots, and optimization of the surface loading of amino groups for high conjugation efficiency and specificity. Another example is modifying the quantum dots with peptides through the amino or carboxyl groups at the terminus, or using other residues, small molecules, proteins, or nucleic acids, and other methods known to those skilled in the art. More specifically, schemes used for the conjugation of antibodies to quantum dots are based on well-known chemistries using the fast and efficient coupling of thiols to maleimide groups, with reactive groups such as primary amines, alcohols, carboxylic acids and thiols used to link the antibodies to the quantum dots.

Quantum dots represent a marked increase in performance over standard organic dyes, because they can be tuned to absorb or emit at any visible or infrared wavelength and can be fabricated into a great variety of forms and media, eliminating completely the shortcomings of dyes. These unique abilities are due to their very small sizes (typically between 1-10 nm in diameter). The small size and its direct relationship to fluorescence also allows for incredible versatility and flexibility of form, letting phosphors match whatever shape their underlying light-emitting diode (LED) needs to assume.

When light impinges on quantum dots, it encounters discretized energy bands specific to the quantum dot. The discretized nature of quantum dot bands means that the energy separation between the valence and conduction bands (the bandgap) can be altered with the addition or the subtraction of just one atom—making for a size dependent bandgap. Pre-determining the size of the quantum dots fixes the emitted photon wavelength at the appropriate customer-specified color, even if it is not naturally occurring—an ability limited only of quantum dots.

Additionally, it is also known that certain rare-earth metal chelates emit visible light upon irradiation with UV light and different forms of visible light (e.g., violet or blue light), an emission which is characterized by the chelated cation. Some lanthanide ions, such as those of europium ($Eu^{3+}$), Samarium ($Sm^{3+}$), terbium ($Tb^{3+}$), and to a lesser extent dysprosium ($Dy^{3+}$) and neodymium ($Nd^{3+}$), exhibit typical fluorescence characterized by the ion, especially when chelated to suitable excitation energy mediating organic ligands. The fluorescent properties of these compounds—long Stokes' shift, narrow band-type emission lines, and unusually long fluorescence lifetimes—have made them attractive candidates for fluorescent immunoassays and time-resolved fluorometric techniques.

The major emission lines of these fluorescent lanthanide chelates are formed from a transition called hypersensitive transition and are around 613-615 nm with $Eu^{3+}$, 545 (and 490) nm with $Tb^{3+}$, 590 and 643 nm with $Sm^{3+}$, and 573 with $Dy^{3+}$. Radiation is typically absorbed by the chelates at a wavelength characteristic of the organic ligand and emitted as a line spectrum characteristic of the metal ion because of an intramolecular energy transfer from the ligand to the central metal ion. The organic ligand absorbs energy and is raised or excited from its singlet ground state, $S_0$, to any one of the vibrational multiplets of the first singlet excited state, $S_1$, where it rapidly loses its excess vibrational energy. At this point, there are two possibilities: relaxation by an $S_1 \rightarrow S_0$ transition (ligand fluorescence) or intersystem crossing to one of the triplet states, $T_1$.

Fluorescent europium chelates are known to exhibit large Stokes shifts (~290 nm) with no overlap between the excitation and emission spectra and very narrow (10-nm bandwidth) emission spectra at 615 nm. In addition, the long fluorescence lifetimes (measurable in microseconds instead of the nanosecond lifetimes measurable for conventional fluorophores) of the chelates help filter out noise and other interference having a low fluorescent lifetime. The long fluorescent lifetimes thus permit use of the chelates for microsecond time-resolved fluorescence measurements, which further reduce the observed background signals. Additional advantages of using europium chelates include that europium chelates are not quenched by oxygen.

In specific binding assays, sensitivity is of prime importance due to the generally low analyte levels that are measured. Radioimmunoassay sensitivity limits the assay to measurements of concentration of $10^{-12}$ M, and more often only in the $10^{-8}$ to $10^{-10}$ M range. In addition, radiolabels suffer from the drawbacks of short half life and handling hazards.

In fluorescence spectroscopy assays, a sample containing a fluorescent species to be analyzed is irradiated with light of known spectral distribution within the excitation spectrum of the target fluorescent species. The intensity of the resulting characteristic emission spectrum of the fluorescent target molecules is determined and is related to the number of target molecules.

The sensitivity of fluorescence assays, although theoretically very high, is limited by the presence of background fluorescence. Background signal levels are picked up from competing fluorescent substances, not only in the sample, but also in materials containing the sample. This is an especially serious problem in quantitative measurements of species associated with samples containing low concentrations of desired target fluorescent molecules such as found in biological fluids. In many situations, it is impossible to reduce the background sufficiently (by appropriate filtration and other techniques known in the art) to obtain the desired sensitivity.

Time resolution offers an independent means of isolating the specific fluorescent signal of interest from nonspecific background fluorescence. Time resolution is possible if the label has much longer-lived fluorescence than the background, and if the system is illuminated by an intermittent light source such that the long-lived label is measurable during the dark period subsequent to the decay of the short-lived background.

Certain fluorescent molecules have been commonly used as tags for detecting an analyte of interest. Organic fluorescent dyes are typically used in this context. However, there are chemical and physical limitations to the use of such dyes. One of these limitations is the variation of excitation wavelengths of different colored dyes. As a result, the simultaneous use of two or more fluorescent tags with different excitation wavelengths requires multiple excitation light sources.

A drawback of organic dyes is the deterioration of fluorescence intensity upon prolonged and/or repeated exposure to excitation light. This fading, called photobleaching, is dependent on the intensity of the excitation light and the duration of the illumination. In addition, conversion of the dye into a nonfluorescent species is irreversible. Furthermore, the degradation products of dyes are organic compounds which may interfere with the biological processes being examined.

Additionally, spectral overlap exists from one dye to another. This is due, in part, to the relatively wide emission spectra of organic dyes and the overlap of the spectra near the tailing region. Few low molecular weight dyes have a combination of a large Stokes shift, which is defined as the separation of the absorption and emission maxima, and high fluorescence output. In addition, low molecular weight dyes may be impractical for some applications because they do not provide a bright enough fluorescent signal.

Furthermore, the differences in the chemical properties of standard organic fluorescent dyes make multiple, parallel assays impractical as different chemical reactions may be involved for each dye used in the variety of applications of fluorescent labels.

Thus, there is a continuing need in the assay art for labels with the following features: (i) high fluorescent intensity (for detection in small quantities), (ii) adequate separation between the absorption and emission frequencies, (iii) good solubility, (iv) ability to be readily linked to other molecules, (v) stability towards harsh conditions and high temperatures, (vi) a symmetric, nearly gaussian emission lineshape for easy deconvolution of multiple colors, and (vii) compatibility with automated analysis. At present, none of the conventional fluorescent labels satisfies all of these requirements.

While fluorescent emissions from functional quantum dot bioconjugates have been used to detect the presence or absence of a target substrate in a sample, at present there remains no fast and effective method and apparatus for measuring SAM and SAH.

SUMMARY OF THE INVENTION

Figure 1:
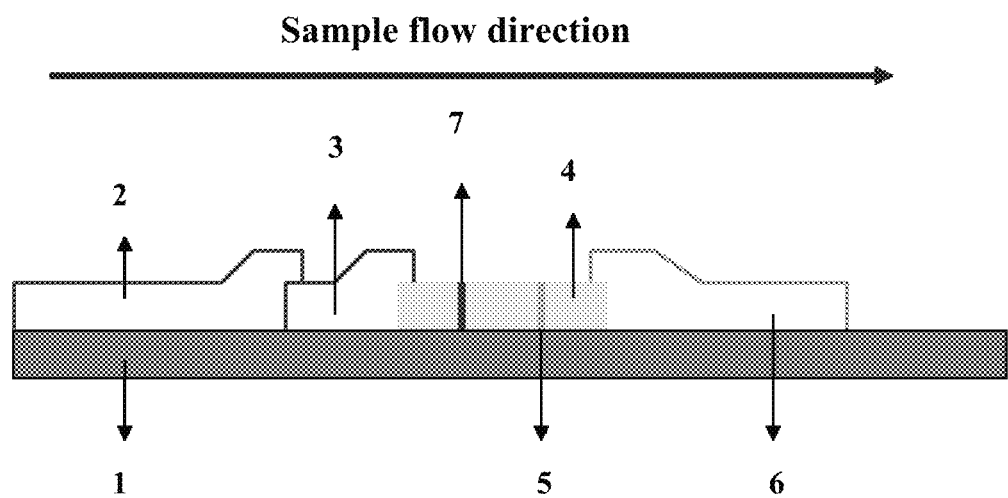
FIG. 1 illustrates two embodiments of the lateral flow immunochromatographic test strips of the invention.
Figure 1:
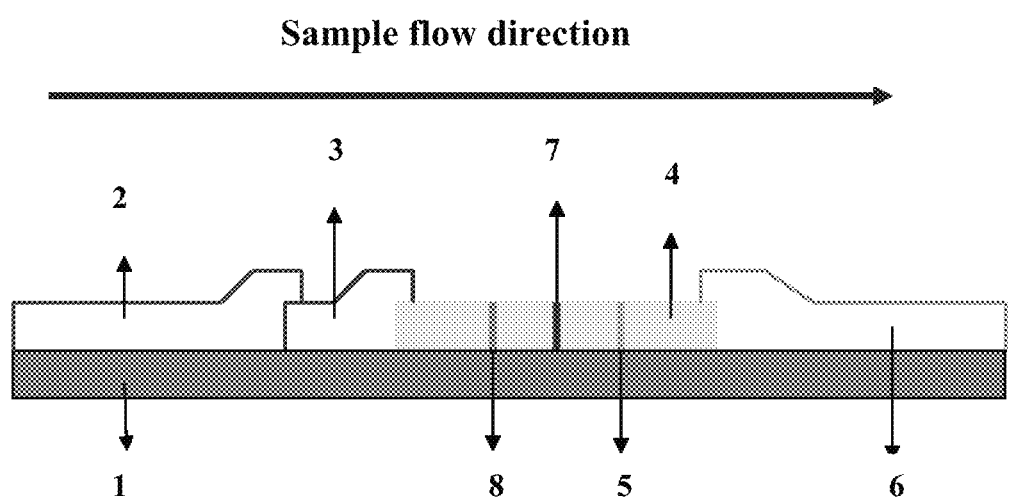

The present invention provides quantum dots having attached thereto an antibody selected from the group consisting of anti-SAM, anti-SAH, anti-HCy and anti-CRP antibodies.

The invention also provides an immunochromatographic strip having incorporated therein quantum dots covalently bonded to anti-SAM, anti-SAH, anti-HCy and anti-CRP antibodies.

The present invention is also directed to the use of quantum dots based immunoassays in combination with chemical methods to measure three closely related biomolecules in a metabolic pathway simultaneously.

The invention is also a method of determining risk of experiencing a major adverse cardiac event in a patient, within one year from presentation of at least one symptom of acute coronary syndrome comprising the steps of: (a) obtaining a test sample from said patient; (b) determining the amount of at SAM, SAH, HCy and optionally C reactive protein using a quantum dot based assay; (c) calculating the MI in said test sample; and d) comparing the amount of said four biomarkers to biomarker reference standards, wherein said risk is determined by results of said comparison.

The invention further provides a method for assaying homocysteine in a sample, said method comprising the steps of: (i) contacting said sample with a homocysteine-converting enzyme that produces SAH and (ii) then measuring SAH using an immunochromatographic strip as described above.

The invention also provides a lateral flow immunoassay test strip for detecting and quantifying the presence of SAM, and SAH alone or simultaneously in a fluid sample, comprising a membrane strip coated with a SAM or SAH-protein conjugate on a test line, and particles conjugated with their antibodies respectively.

The invention is also directed to a fluorescent lanthanide chelate conjugated to an antibody selected from the group consisting of anti-SAM, anti-SAH, and anti-CRP antibodies and use of the conjugates in making immunochromatographic strips.

The invention further provides a method of detecting and quantifying SAM and SAH in a sample, comprising: (a) providing a sample containing or suspected of containing SAM and SAH on a solid support; (b) combining said sample with a semiconductor nanocrystal anti SAM antibody and anti SAH antibody conjugate, wherein said combining is performed under conditions that allow formation of a complex comprising said conjugate and said SAM and SAH, when present; (c) removing any unbound conjugate; and (d) detecting the presence of the complex, if present, by monitoring a spectral emission mediated by the semiconductor nanocrystal in the complex, wherein the emission indicates the presence and quantity of SAM and SAH in the sample.

The invention further relates to the use of a SAM immuno-chromatographic strip to determine and monitor the levels of SAM in patients afflicted with a disease selected from the group consisting of depression, osteoarthritis, liver and gall bladder diseases and then proposing a therapeutic regimes for administering S-Adenosyl-methionine.

The invention also provides a method for determining the effectiveness of a diet program for administration to a patient having at least one diet-responsive condition comprising the steps of: (a) selecting a plurality of patients, each having at least one diet-responsive condition; (b) identifying in said patient the body mass index (BMI) and at least one other quantifiable indicator selected from methylation index and SAM levels for each of said diet-responsive conditions and measuring said at least one indicator for each of said patients during a baseline period; (c) monitoring each of said patients during said baseline period to determine a baseline quality of life; (d) dividing said plurality of patients randomly between a first group and a second group; (e) administering said diet program to each of said patients in said first group during an intervention period; (f) maintaining each of said patients in said second group on a control diet with known beneficial effects on said at least one diet-responsive condition during said intervention period; and (g) monitoring said at least one indicator of each of said conditions for each of said patients after said intervention period.

EMBODIMENTS OF THE INVENTION

In the present invention the term "semiconductor nanocrystal," and "quantum dot" are used interchangeably herein and refer to an inorganic crystallite between about 1 nm and about 1000 nm in diameter or any integer or fraction of an integer therebetween, preferably between about 2 nm and about 50 nm or any integer or fraction of an integer therebetween, more preferably about 2 nm to about 20 nm (such as about 2, 3, 4, 5, 6, 7, 8, 9, 10, 11, 12, 13, 14, 15, 16, 17, 18, 19, or 20 nm). A semiconductor nanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

A semiconductor nanocrystal is, optionally, surrounded by a "coat" of an organic capping agent. The organic capping agent may be any number of materials, but has an affinity for the semiconductor nanocrystal surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanocrystal homogeneously into a chosen solvent, functionality, binding properties, or the like. In addition, the coat can be used to tailor the optical properties of the semiconductor nanocrystal. Methods for producing capped semiconductor nanocrystals are discussed further below.

The term "antibody" as used herein includes antibodies obtained from both polyclonal and monoclonal preparations, as well as, hybrid (chimeric) antibody and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas.

A semiconductor nanocrystal is "linked" or "conjugated" to, or "associated" with, a specific-binding molecule or member of a binding pair when the semiconductor nanocrystal is chemically coupled to, or associated with the specific-binding molecule. Thus, these terms intend that the semiconductor nanocrystal may either be directly linked to the specific-binding molecule or may be linked via a linker moiety, such as via a chemical linker described below. The terms indicate items that are physically linked by, for example, covalent chemical bonds, physical forces such van der Waals or hydrophobic interactions, encapsulation, embedding, or the like. As an example without limiting the scope of the invention, nanocrystals can be conjugated to molecules that can interact physically with biological compounds such as cells, proteins, nucleic acids, subcellular organelles and other subcellular components. For example, nanocrystals can be associated with biotin which can bind to the proteins, avidin and streptavidin As used herein, a "biological sample" refers to a sample of isolated cells, tissue or fluid, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

A "small molecule" is defined as including an organic or inorganic compound either synthesized in the laboratory or found in nature. Typically, a small molecule is characterized in that it contains several carbon-carbon bonds, and has a molecular weight of less than 1500 grams/Mol.

In its broadest aspect, the present invention provides a composition that can provide information about a biological state or event associated with S-adenosylmethionine, S-adenosylhomocysteine and homocysteine and C-reactive protein. The composition by way of example can detect the presence or amounts of the above molecules.

The composition is comprised of a fluorescent semiconductor nanocrystal (also known as a Quantum Dot) having a characteristic spectral emission, which is tunable to a desired energy by selection of the particle size, size distribution and composition of the semiconductor nanocrystal. The composition further comprises a compound i.e., an antibody against SAM or SAH associated with the semiconductor nanocrystal that has an affinity for the biological target.

The composition interacts or associates with a biological target due to the affinity of the compound with the target. Location and nature of the association can be detected by monitoring the emission of the semiconductor nanocrystal.

In operation, the composition is introduced into an environment containing a biological target and the composition associates with the target. The composition:target complex may be spectroscopically view or otherwise detected, for example, by irradiation of the complex with an excitation light source. The semiconductor nanocrystal emits a characteristic emission spectrum which can be observed and measured, for example, spectroscopically.

As an advantage of the composition of the present invention, the emission spectra of a population of semiconductor nanocrystals have linewidths as narrow as 25-30 nm, depending on the size distribution heterogeniety of the sample population, and lineshapes that are symmetric, gaussian or nearly gaussian with an absence of a tailing region. The combination of tunability, narrow linewidths, and symmetric emission spectra without a tailing region provides for high resolution of multiply-sized nanocrystals, e.g., populations of monodisperse semiconductor nanocrystals having multiple distinct size distributions, within a system and enables researchers to examine simultaneously a variety of biological moieties, e.g., target analytes, tagged with nanocrystals.

In addition, the range of excitation wavelengths of the nanocrystals is broad and can be higher in energy than the emission wavelengths of all available semiconductor nanocrystals. Consequently, this allows the simultaneous excitation of all populations of semiconductor nanocrystals in a system having distinct emission spectra with a single light source, usually in the ultraviolet or blue region of the spectrum. Semiconductor nanocrystals are also more robust than conventional organic fluorescent dyes and are more resistant to photobleaching than the organic dyes. The robustness of the nanocrystal also alleviates the problem of contamination of the degradation products of the organic dyes in the system being examined. Therefore, the present invention provides uniquely valuable tags for detection of biological molecules and the interactions they undergo.

In one preferred embodiment, the composition comprises semiconductor nanocrystals associated with molecules that can physically interact with biological compounds. Without limiting the scope of the invention, molecules include ones that can bind to proteins, nucleic acids, cells, subcellular organelles, and other biological molecules. The compound used in the composition of the present invention preferably has an affinity for a biological target. In some preferred embodiments, the compound has a specific affinity for a biological target. The affinity may be based upon any inherent properties of the compound, such as without limitation, van der Waals attraction, hydrophilic attractions, ionic, covalent, electrostatic or magnetic attraction of the compound to a biological target. As used herein, "biological target" is meant any moiety, compound, cellular or subcellular component which is associated with biological functions. The biological target includes without limitation proteins, nucleic acids, cells, subcellular organelles and other biological moieties.

The ability to use semiconductor nanocrystals in order to detect multiple targets results from their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies).

The optical properties of quantum dots are primarily dictated by their physical size and chemistry. Typically, electromagnetic radiation having a wavelength within the visible light and infrared portions of the spectrum will excite quantum dots. The absorption spectrum of a quantum dot appears as a series of overlapping peaks that become increasingly larger at decreasingly shorter wavelengths. Each peak corresponds to an energy transition between discrete electron-hole energy states (exciton) within the quantum dot. The size of a quantum dot and the difference between its energy states are inversely proportional. Thus, the difference between energy states of larger quantum dots is smaller than the difference between energy states of smaller quantum dots. The size of the quantum dots of the invention are in the range of 2-10 nm.

The smaller the difference between the energy states of a quantum dot, the "redder" (or higher wavelength) of the electromagnetic radiation (e.g., light) emitted therefrom. Thus, when excited, larger quantum dots will emit "redder" light than smaller quantum dots, which will emit "bluer" light. As a consequence of these phenomena, the wavelength of electromagnetic radiation emitted by a quantum dot may be tailored by selecting the material from which the quantum dot is to be synthesized and the size to which the quantum dot is to be synthesized. When excited, known quantum dots may emit electromagnetic radiation (e.g., light) having a wavelength from about 490 nm (blue) to about 705 nm (red).

Quantum dots have high quantum yields and resist photobleaching; their use therefore providing for very sensitive fluorescent biological assays. Different types of quantum dots are excited when exposed to different ranges of wavelengths of electromagnetic radiation. Currently available quantum dots may be excited by electromagnetic radiation having wavelengths as low as about 300 nm and as high as about 2,300 nm.

It is currently preferred that the markers within reagent solution have a Stoke's shift of about 50 nm or greater (e.g., the difference between excitation of the marker at about 658 nm and emission at about 703 nm) or even of about 100 nm or greater (e.g., quantum dots that are excited at about 405 nm may emit radiation having a wavelength of about 530 nm).

Upon exposure to a primary light source, each semiconductor nanocrystal distribution is capable of emitting energy in narrow spectral linewidths, as narrow as 12 nm to 60 nm, and with a symmetric, nearly Gaussian line shape, thus providing an easy way to identify a particular semiconductor nanocrystal. It should be noted that the linewidths are dependent on the size heterogeneity, i.e., monodispersity, of the semiconductor nanocrystals in each preparation. In addition, semiconductor nanocrystal distributions with larger linewidths in the range of 35 nm to 60 nm can be readily made and have the same physical characteristics as semiconductor nanocrystals with narrower linewidths.

The present invention uses a composition comprising semiconductor nanocrystals associated with a specific-binding molecule or affinity molecule, such that the composition can detect the presence and/or amounts of biological and chemical compounds, detect interactions in biological systems, detect biological processes, detect alterations in biological processes, or detect alterations in the structure of biological compounds. Without limitation, semiconductor nanocrystal conjugates comprise any molecule or molecular complex, linked to a semiconductor nanocrystal, that can interact with a biological target, to detect biological processes, or reactions, as well as alter biological molecules or processes. Preferably, the molecules or molecular complexes or conjugates physically interact with a biological compound. Preferably, the interactions are specific. The interactions can be, but are not limited to, covalent, noncovalent, hydrophobic, hydrophilic, electrostatic, van der Waals, or magnetic. Preferably, these molecules are small molecules, proteins, or nucleic acids or combinations thereof.

Semiconductor nanocrystal conjugates can be made using techniques known in the art. For example, moieties generally used in the production of semiconductor nanocrystals, as well as other moieties, may be readily displaced and replaced with other functional moieties, including, but not limited to carboxylic acids, amines, aldehydes, and styrene to name a few. One of ordinary skill in the art will realize that factors relevant to the success of a particular displacement reaction include the concentration of the replacement moiety, temperature and reactivity. Thus, for the purposes of the present invention, any functional moiety may be utilized that is capable of displacing an existing functional moiety to provide a semiconductor nanocrystal with a modified functionality for a specific use.

The ability to utilize a general displacement reaction to modify selectively the surface functionality of the semiconductor nanocrystals enables functionalization for specific uses. For example, because detection of biological compounds is most preferably carried out in aqueous media, a preferred embodiment of the present invention utilizes semiconductor nanocrystals that are solubilized in water. In the case of water-soluble semiconductor nanocrystals, the outer layer includes a compound having at least one linking moiety that attaches to the surface of the particle and that terminates in at least one hydrophilic moiety. The linking and hydrophilic moieties are spanned by a hydrophobic region sufficient to prevent charge transfer across the region. The hydrophobic region also provides a "pseudo-hydrophobic" environment for the nanocrystal and thereby shields it from aqueous surroundings. The hydrophilic moiety may be a polar or charged (positive or negative) group. The polarity or charge of the group provides the necessary hydrophilic interactions with water to provide stable solutions or suspensions of the semiconductor nanocrystal. Exemplary hydrophilic groups include polar groups such as hydroxides (—OH), amines, polyethers, such as polyethylene glycol and the like, as well as charged groups, such as carboxylates (—$CO_2^-$), sulfonates ($SO_3^-$), phosphates (—$PO_4^{2-}$ and —$PO_3^{2-}$), nitrates, ammonium salts (—$NH_4^+$), and the like. A water-solubilizing layer is found at the outer surface of the overcoating layer.

A displacement reaction may be employed to modify the semiconductor nanocrystal to improve the solubility in a particular organic solvent. For example, if it is desired to associate the semiconductor nanocrystals with a particular solvent or liquid, such as pyridine, the surface can be specifically modified with pyridine or pyridine-like moieties to ensure solvation.

The surface layer may also be modified by displacement to render the semiconductor nanocrystal reactive for a particular coupling reaction. For example, displacement of certain moieties with a group containing a carboxylic acid moiety enables the reaction of the modified semiconductor nanocrystals with amine containing moieties (commonly found on solid support units) to provide an amide linkage. Additional modifications can also be made such that the semiconductor nanocrystal can be associated with almost any solid support. A solid support, for the purposes of this invention, is defined as an insoluble material to which compounds are attached during a synthesis sequence, screening, immunoassays, etc. The use of a solid support is particularly advantageous for the synthesis of libraries because the isolation of support-bound reaction products can be accomplished simply by washing away reagents from the support-bound material and therefore the reaction can be driven to completion by the use of excess reagents.

A solid support can be any material that is an insoluble matrix and can have a rigid or semi-rigid surface. Exemplary solid supports include but are not limited to pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N—N'-bis-acryloyl-ethylenediamine, and glass particles coated with a hydrophobic polymer.

For example, the semiconductor nanocrystals of the present invention can readily be functionalized to create styrene or acrylate moieties, thus enabling the incorporation of the semiconductor nanocrystals into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

The test strips of our invention have the configuration as shown in FIG. 1. Referring to embodiment A of FIG. 1, element 1 is a PVC plate incorporating a sample pad 2 for antibody conjugate layer 3. The test device further includes an absorption zone 7 which is typically paper and a nitrocellulose membrane 4 which includes a control band 5 and a test band 7.

In embodiment B of FIG. 1, the construction is similar to the test device A however it includes another test band 8 for either SAM or S-Adenosylhomocysteine.

The test strip of embodiment A of FIG. 1, includes one test band and one control band. The test strip of embodiment B of FIG. 1 includes two test bands for SAM and SAH respectively (i.e. Methylation Index (MI) strip). The diagram of FIG. 1 shows how each component is assembled (lateral view). Liquid samples are applied through the left side of the sample pad, and the sample immediately migrates in the sample flow direction as shown in FIG. 1. The results are ready to be read in about 15 minutes after sample application to the strips.

Numerous variations of the strip of FIG. 1 are possible. But the basic construction of an immunochromatographic strip is as follows and some of the different elements of the strip are optional and used as required depending on the needs of the tests.

The following describes certain elements that form part of assay devices according to the present invention. Although the elements can be placed in various arrangements, according to the assay format intended and the type of assay to be carried out, in general, the characteristics of the elements defined herein do not change between one arrangement and another. As used herein, the elements described can be in any suitable physical form for the purposes of assay devices according to the present invention, such as, but not limited to, membranes, pads, strips, or other physical forms.

A. Chromatographic Strip

As used in assay devices according to the present invention, the chromatographic strip can be composed of any suitable material that has a high protein binding capability and supports a lateral flow assay. Typically, the chromatographic strip is a hydrophilic element and the protein binding is through noncovalent binding. Although Applicants do not intend to be bound by this theory, current theory of binding of proteins to nitrocellulose states that the initial interaction is electrostatic, but subsequently hydrophobic interactions and hydrogen bonds considerably strengthen the binding. An example of a chromatographic material is the commonly used nitrocellulose element, which has been treated to make it hydrophilic. Another example of a chromatographic element is one made up of particles of a polymer, such as polyethylene, fused together. The chromatographic strip is of any size appropriate for the instrument or device used to read the results or for being read visually.

When antigens or antibodies are coated onto the chromatographic strip, due to its porous nature, the protein solution distributes itself throughout the depth of the nitrocellulose element. The proteins bind to the pore surfaces. Because of the method of application and the physics of the binding, more protein is bound to the top and center of the line compared to other areas wetted by the solution used to coat the antigens or antibodies onto the chromatographic strip.

The chromatographic strip as used in assay devices according to the present invention includes a capture band, described further below. The chromatographic strip also typically includes one or more control bands, also described further below.

The chromatographic strip of the present invention contains at least one capture band for capturing the analyte and at least one control band and, optionally, a second control band. When used in conjunction with a cassette, the capture band, and the control band or bands can be viewed through a testing window. The capture band contains materials that are capable of capturing an analyte in a sample if the analyte is present. For example, if the lateral flow assay is intended to measure SAM in a biological sample, the capture band will contain antibody to SAM immobilized on the chromatographic strip at the capture band. The chromatographic strip will additionally contain conjugates or detectable agents at the second end for detecting the captured analyte.

B. Sample Filter

Assay devices according to the present invention may employ a sample filter (in some cases, two sample filters). The location of the sample filter or sample filters can vary, but the sample filter is situated so that fluid present in a sample, when applied onto the sample filter will flow from the sample filter to the chromatographic strip, either directly or indirectly. The sample filter is, in one alternative, a hydrophobic element, or alternatively a hydrophilic element or a synthetic composite of such as typically used in lateral flow assays for sample application. Examples of such sample filters include, but are not limited to hydrophobic filters such as glass fiber filters and hydrophilic filters such as cellulose.

C. Sample Pad

In some applications, particularly when the sample does not require the removal of cells or other large particles, a sample pad can replace the sample filter. The term "sample pad" refers to a hydrophobic element, such as a hydrophobic element, that can be used to receive a sample.

D. Conjugate Pad

The term "conjugate pad" is used to describe an element that is used in many embodiments of assay devices according to the present invention. The conjugate pad is composed of a hydrophobic material, such as glass fiber and contains a conjugate or a detectable agent that can react with an analyte in a sample or with an analyte that is captured on the capture band on the chromatographic strip. The detectable agent includes, for example, antibodies or antigens specific for the analyte that are conjugated to a detectable material such as a colored material, a fluorescent material, or a chemiluminescent material or a quantum dot. An example of a colored material is colloidal gold. The conjugate pad herein is of a size suitable for the chromatographic strip within the parameters described. The conjugate pads can be preblocked with a buffer solution containing trehalose and casein, although other buffer solutions can alternatively be used for preblocking. Use of the conjugate pad is not necessarily required in all embodiments of assay devices according to the present invention. In some alternatives, the conjugate pad is omitted, and the conjugate is applied to the chromatographic strip. These alternatives are described further below.

E. Fluid Collector

The term "fluid collector" is used to describe an element used in some configurations of assay devices according to the present invention. The fluid collector is typically a hydrophobic element, just like the hydrophobic element of the conjugate pad. Unlike the conjugate pad, the fluid collector does not contain any detectable agents and is used as an intermediate element, typically to transmit fluid, directly or indirectly, to the chromatographic strip.

F. Capture Band

As described above, the test strip always includes at least one capture band. The term "capture band" as used herein refers to a region or zone on the chromatographic strip that contains at least one analyte binding agent. The analyte binding agent is usually immobilized in a band or zone such that after reaction with a detectable agent, the band or zone produces an observable or measurable result reflecting the presence or amount of analyte present in the sample. The "capture band" may be comprised of more than one capture zone for capturing more than one analyte in the sample, in which event, more than one analyte binding agent may be used. For example, two assay combinations that are considered to be within the scope of the invention as shown in the examples.

G. Control Band

Typically, the chromatographic strip of a device according to the present invention also includes one or more control bands, which contain control agents immobilized in control binding zones.

H. Buffer Pad

Some embodiments of assay devices according to the present invention employ a buffer pad. The buffer pad is a hydrophilic element or a synthetic composite. The buffer pad is of a size suitable for the chromatographic strip within the parameters described.

I. Absorbent Pad or Pads

Typically, assay devices according to the present invention include one or more absorbent pads. These absorbent pads serve to direct fluid flow within the device. The size and location of these absorbent pads largely determines the flow pattern, as described above. The absorbent pad is a hydrophilic element that can absorb liquid, such as or a cellulose-glass fiber composite. The absorbent pad herein is of a size suitable for the chromatographic strip within the parameters described.

J. Backing Pad

Some assay devices according to the present invention include a backing pad that serves as a backing for the chromatographic strip. The backing pad can be made of any inert material that is capable of supporting the chromatographic strip, such as a piece of plastic material The size of the backing pad is suitable for the chromatographic strip within the parameters described.

K. Fluid-Impermeable Barrier

Some embodiments of assay devices according to the present invention incorporate a fluid-impermeable barrier interposed between elements such as a sample filter at or near the first end of the chromatographic strip and the chromatographic strip itself.

In a preferred embodiment of the invention, immunoassays, such as ELISA (Enzyme-linked Immunosorbent Assay) for determining qualitatively and quantitatively the concentration of SAM and SAH in a biological sample, are provided in which semiconductor nanocrystal conjugates are used as the detection reagents. The immunosorbent assay of the present invention has several advantages over current immunosorbent assays including, but not limited to, simultaneous multicolor detection and, hence, multiple analyte detection, with no requirement for enzyme development, increased photostability over alternative fluorophores thereby allowing increased detection sensitivity by virtue of the ability to monitor the signal over a long period of time, increased sensitivity over enzyme-based detection systems.

Semiconductor nanocrystals of varying core sizes (10-150 .ANG.), composition and/or size distribution are conjugated to specific-binding molecules which bind specifically to SAM and SAH. Any specific anti-analyte can be used, for example, an antibody, an immunoreactive fragment of an antibody, and the like. Preferably, the anti-analyte is an antibody. The semiconductor nanocrystal conjugates are used in an immunosorbent assay to detect any analyte for which a specific-binding agent exists.

More specifically, the specific-binding molecule may be derived from polyclonal or monoclonal antibody preparations, may be a human antibody, or may be a hybrid or chimeric antibody, such as a humanized antibody, an altered antibody, F(ab').sub.2 fragments, F(ab) fragments, Fv fragments, a single-domain antibody, a dimeric or trimeric antibody fragment construct, a minibody, or functional fragments thereof which bind to the analyte of interest.

In this invention, we have combined together as a single unit immunochromatographic and photochemical test strips for the simultaneous measurement of three critical molecules in methionine cycles, i.e. SAM, SAH and HCy, which have been reported to be very important in understanding the dynamics and health status of related biochemical pathways as well as act as IVD biomarkers. The invention also deals with a new device that facilitates the aforementioned invention for the purpose of POCT uses. The spectrometer used in the invention is a combination of a fluorescence spectrometer and an absorbance UV/VIS spectrometer.

In another embodiment, the invention provides a method of determining risk of experiencing a major adverse cardiac event, in a patient, within one year from presentation of at least one symptom of acute coronary syndrome comprising the steps of: (a) obtaining a test sample from said patient; (b) determining the amount of at SAM, SAH, HCy and C reactive protein using a quantum dot based assay employing an immunochromatographic strip; (c) calculating the MI in said test sample; and c) comparing the amount of said four biomarkers to biomarker reference standards, wherein said risk is determined by results of said comparison.

By way of example, the preparation and assemblage of the immunoassay test immunochromatographic strip is done as follows. Briefly, goat anti-mouse IgG and BSA-SAH were separately applied to NCM (2.5×2.0 cm) with 3.5 μg in 10 mM phosphate-buffered saline, pH 7.4, to be used as the control zone and the test zone. The distance between the control zone and the test zone was 0.5 cm. The NCM was then dried for 1.5 hours at 37° C. to fix the antibody and antigen. The NCM was pasted onto the polyvinyl chloride strip with the adsorption pad on the top end, and the quantum dot-conjugated pad overlapped by the sample pad was adhered to the bottom end of the NCM. The quantum dot-conjugated pad had been prepared by adding the anti-SAH MoAb-coated quantum dots (i.e, CdSeNPs) to the glass fiber (2.5×1.0 cm). The resultant conjugated pad was incubated at 37° C. for 1.5 hours until fully dried. The sample pad of glass fiber (2.5×2.0 cm) was submerged in 10 mM phosphate-buffered saline, pH 7.4 and containing 0.05% Tween 20, and dried at 37° C. for 1.5 hours. Finally, the test device was cut into 5 mm-wide strips and stored at RT before use.

When using lanthanide based fluorescent molecules, the SAM or SAH binding antibody is conjugated with a fluorescent label such as, without limitation, the rare earth chelates (e.g., europium chelates). The fluorescent labels can be conjugated to the antibody using conventional techniques in immunology. Fluorescence can be quantified using a fluorimeter or UV/vis spectrophotometer using the known extinction coefficient of the fluorescent label.

The fluorescence properties of certain lanthanide chelates, especially chelates of europium and terbium, are well suited fluorescent markers. The absorbance of these chelates is very strong, (more than $10^4$) and dependent upon the ligands. Although the quantum yield is often smaller than that for organic markers these chelates have other advantages, thus the emission appears at relatively long wavelengths (terbium 544 nm, europium 613 nm) in which wavelength range the serum fluorescence is low and furthermore the excitation maximum is within the short UV-range (Terbium-chelates 270-320 nm, Eu-chelates 320-360 nm) independent of the ligands which makes it possible to excite them with lamps or lasers commercially available and furthermore the Stoke's shift is very long (240-270 nm) and the emission band is sharply limited which enables a small band width. The most essential property is however that the fluorescence time is long, about 50-1000 microseconds which makes it possible to use the above mentioned instrumentation. As the fluorescence is measured with a certain delay during which the background fluorescence has decayed, the effect of an unspecific background radiation can be eliminated.

The chelates of europium and to a certain extent terbium together with different .beta.-diketones are the most used chelates due to their ability to laser in different solutions and at different temperatures. The most widely used β-diketones are benzoylacetone (BA), dibenzoylmetane (DBM), thenoyltrifluoroacetone (TTA), benzoyltrifluoroacetone (BTA), 1- and 2-naphihoyltrifluoroacetone (1-/2-NTA), acetylaceton (AcA), trifluoroacetylacetone (TFAcA), and hexafluoroacetylacetone (HFAcA).

The strong fluorescence of the lanthanide chelates is due to the absorption by the ligands of the excitation radiation and of the energy transfer from the triplet state of the ligand which gives rise to a narrow band radiation with a long wavelength characteristic for metals.

Before a chelate of the above mentioned type could be used as a fluorescent marker it has to be attached to the antibody/antigen to be investigated. Furthermore, the metal has to give a fluorescent radiation also after the binding and in a water solution. To be stable enough, also in very diluted form (even below $10^9$ M) and under conditions where other chelate forming reagents are present as well as an excess of other metal ions, the binding system must be very strong. The stability constant of the chelate must be well above $10^{10}$ and additionally the binding ligand has to leave coordination positions free for another bidentate ligand.

By way of further background into the present invention, given the important roles of SAM, SAH, HCy and C-reactive proteins in various pathological processes, it is desirable to conveniently measure the levels of SAM, SAH, HCy and C-reactive protein using the methods that can be done in common research and clinical labs. With the availability of specific antibodies against SAM, SAH and C-reactive protein various forms of immunoassays using immunochromatographic test strips are extremely useful in the clinical environment. Having a test strip that measures SAM, SAH, HCy and C-reactive protein would be an ideal addition to the clinical lab.

Figure 7:
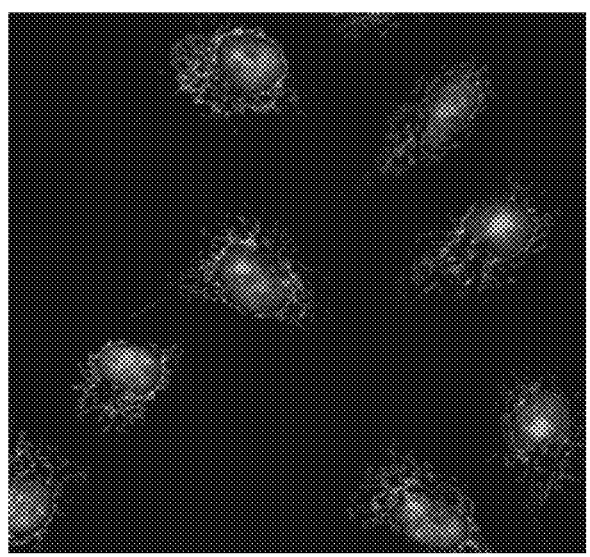
FIG. 7 illustrates the Laser Scan Confocal Microscopy (LSCM) results of L02 and HepG2 cells that were cultured for 40 h and then stained with the same fluorescence labelled anti-SAM and anti-SAH antibodies of the invention.
Figure 7:
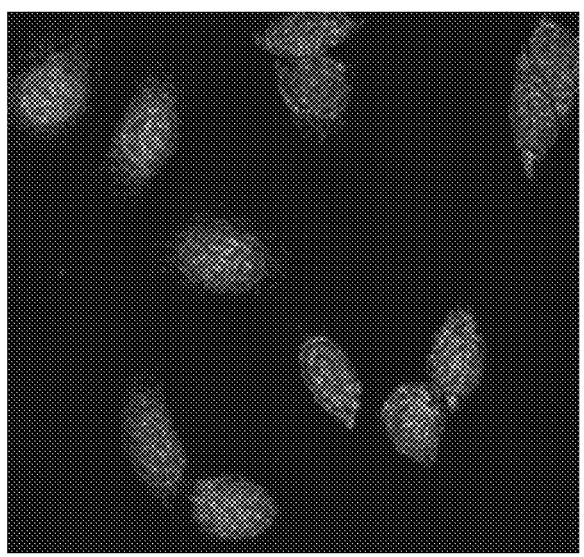
Figure 7:
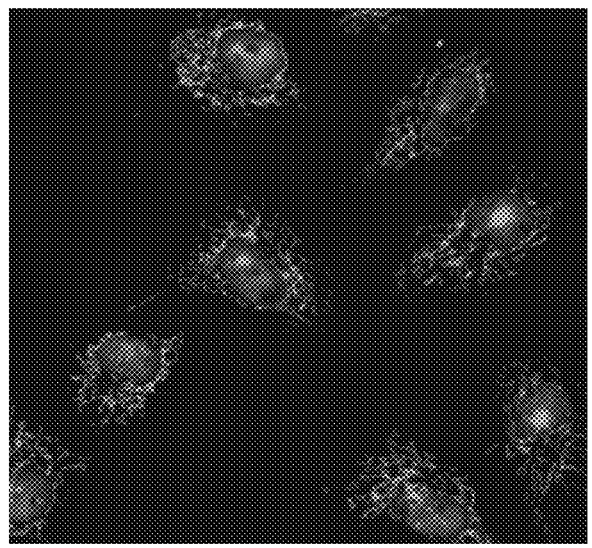
Figure 7:
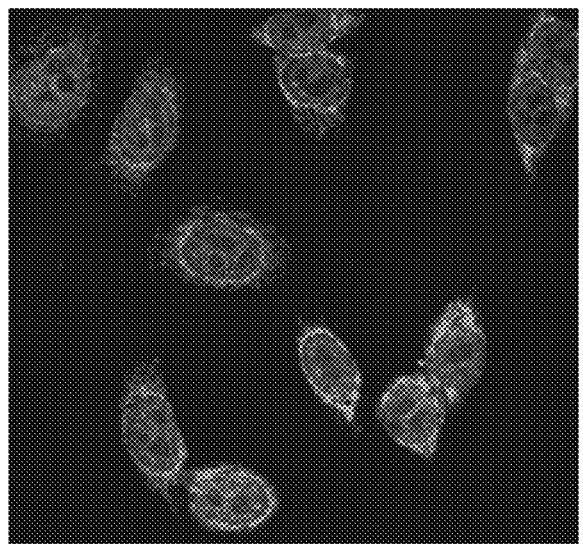

In a further embodiment of the invention, with the fluorescence-labeled anti-SAM and anti-SAH antibodies of the invention that have been proven to be specific, quick and easy measurements of SAM and SAH can be performed at the cellular level via flow cytometry, immunofluorescence microscopy or LSCM. The immunofluorescence microscopy has the advantage of studying the levels and locations of SAM and SAH even with a small number of cells, e.g. studying SAM and SAH from cells in their early stages of embryo development with a couple of hundreds of cells or even less. The LSCM results from FIG. 7 showed that intracellular localizations of SAM and SAH were somewhat similar. SAM and SAH were seen mostly in mitochondria, peri-nuclei and in nucleoli. In HepG2 cells cultured for 40 h, compared to L02, obviously reduced levels of SAM and SAH were observed in cytoplasm, slightly more SAH and SAM in nuclei (consistent with FCM results from FIG. 5) yet they were not focused in nucleoli area as L02 cells were.

Figure 8:
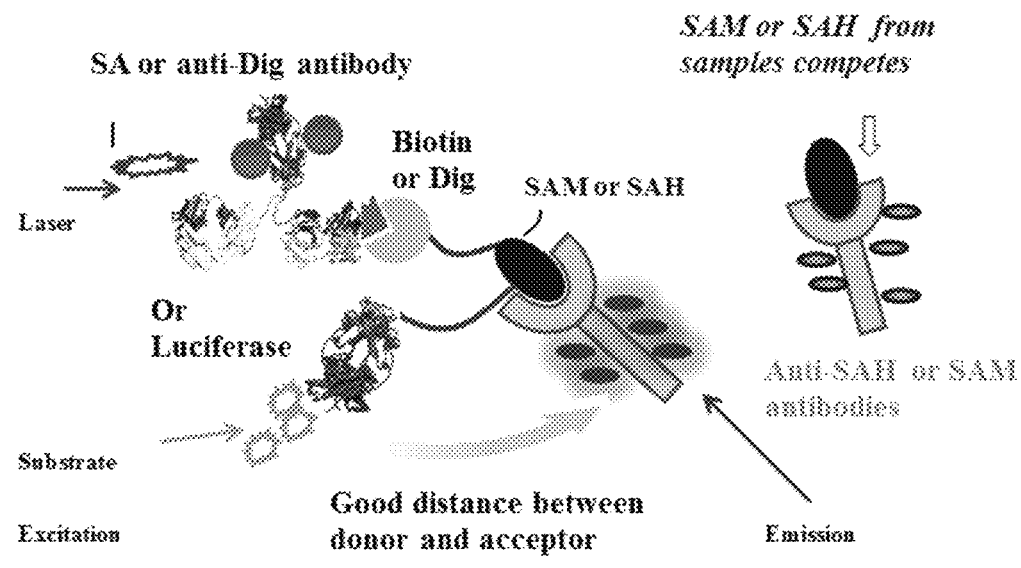
FIG. 8 shows simple diagrams illustrating how the two formats of TR-FRET technology may be used to quantitatively measure SAM and SAH using the bio-conjugates described in this invention.
Figure 8:
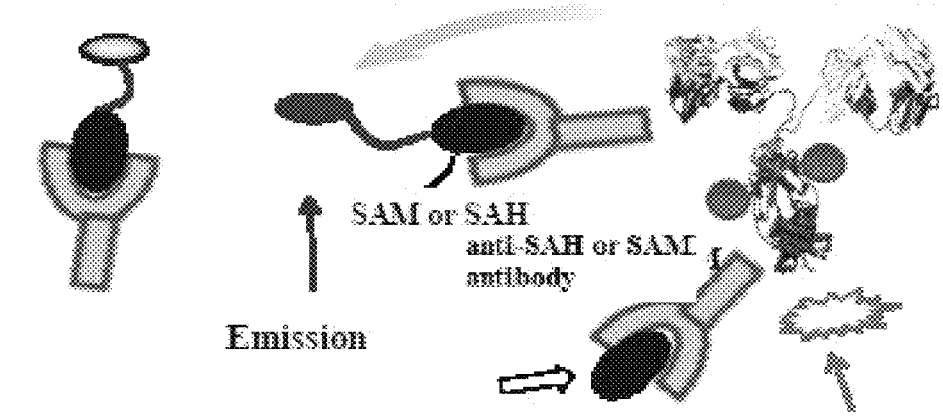

The invention also provides an easy and quick homogeneous immunoassay that does not have special strip preparation as well as no washing and separation steps that can also be used conveniently in the point-of-care test (POCT) setting besides the commonly known dry test strips. FIG. 8 show simple diagrams illustrating how the two formats of TR-FRET technology may be used in the quantitative measurement of SAM and SAH using the bio-conjugates described in this invention. With format A of FIG. 8, specific antibodies against SAM or SAH are associated with acceptor dyes directly or indirectly through rabbit or goat anti-mouse IgG that is labeled with acceptor dye. Two tracing methods, SA-biotin and Dig-anti-digoxin antibody specific binding partners, are shown that are conjugated to donor dyes. The biotin-conjugated (or Dig-conjugated) SAM or SAH with different linkers brings donor and acceptor dyes together in close proximity, most likely less than 100 angstrom (Å), which allows the donors to excite the acceptor dyes. The energy transfer with the donors occurs and a distinguished fluorescence emitted at a specific wave length from acceptor dyes is measured that reflects only the portion of the molecules that are able to connect donors and acceptors together specifically. Free SAM or SAH molecules from a sample compete with the bio-conjugates for binding the anti-SAM or anti-SAH antibodies, therefore lead to reduced fluorescent signals. Competitive measurement can be established based on the competitive binding characteristics.

With format B of FIG. 8 SAM, SAM analog or SAH is conjugated (with or without a linker) to an acceptor dye, which will compete with free SAM or SAH from samples for binding to the antibodies against SAM or SAH that are attached to donor indirectly through rabbit or goat anti-mouse IgG. The emitted fluorescence from acceptor dyes reflects the amounts of SAM or SAH bound to the donor dyes that are not competed by the SAM or SAH in the samples, i.e. donor-specific antibody-antigen-acceptor complex. The amount of specific antibodies that bind to un-conjugated SAM or SAH molecules will not have fluorescence to be read, which constitutes one of the competing parties in the competitive assay. Free anti-SAM or SAH antibody, if any, which is not conjugated with donor dyes, will consume either labeled or unlabeled antigens. Both donor and acceptor fluorescence signals are read with the TR-FRET microplate reader and the acceptor fluorescence/donor fluorescence can be calculated that will be used in quantifying SAM or SAH from a sample.

BRET (Bioluminescence Resonance Energy Transfer) technology is similar to TR-FRET or FRET except for the donor dye is replaced with bioluminenscent enzyme, e.g. luciferase (EC1.13.12.7) or Luc. The acceptor dye should be chosen so that it has an optimal spectral overlap between the Luc bioluminescent spectra and the dye excitation spectra and higher quantum yield. For example, SAM or SAH (antigen) is conjugated to Luc, the fluorescent dye that meets the criteria above is conjugated to the anti-SAM or anti-SAH antibody. Addition of firefly luciferin, a Luc substrate, causes luciferin to luminescence and meanwhile excites acceptor dyes to emit fluorescence when Luc-antigen-antibody-acceptor dye complex is formed. Both donor luminescence and acceptor fluorescence are recorded and BRET index (acceptor fluorescence/donor luminescence) can be calculated. The more the SAM or SAH antigens from a sample are present, the less the acceptor fluorescence, thereby the less the BRET index.

Competitive BRET homogeneous immunoassay can be established to quantify SAM or SAH after optimizing every condition so the linearity, sensitivity, recoverability and reproducibility are satisfactory. A part of the FIG. 8A also illustrates how this process works. The BRET-based method does not require laser excitation of donor dye at the time of detection. Instead it only needs to add the substrate of the luciferase. When enough substrates start to generate luminescence that can be measured, it also excites the acceptor fluorescent materials that are brought to its close proximity by specific antigen-antibody. It does not excite acceptor fluorescent dyes that are not associated with luciferase donor. Therefore, the emission signals measured reflect the part of antigen-antibody complex containing both the donors (bio-conjugates) and acceptors, not the SAM or SAH antigens from samples or standards that are only associated with acceptors via antibodies.

EXAMPLES

The following examples are intended to demonstrate the usefulness of the methods and compositions of the present invention and should not be construed to limit the scope of the invention in anyway. In the present specification the term biological sample is intended to include saliva, urine, blood, serum, plasma, brain fluids, cerebrospinal fluids, tissue samples and cells or anything derived from the body of a mammal including a human.

The quantum dots (CdTe/CdSe, CdHgTe/ZnS, etc.) with mean diameter of 2-10 nm were purchased from NN-Labs, LLC (Fayetteville, Ark. 72701). Fluorescent dye Europium chelates or other lanthanide metals, etc. with mean diameter at 200 nm-300 nm were purchased from Bangslab (Fishers, Ind. 46038). In the context of the present specification we refer to the lanthanides fluorescent dyes and quantum dots to as fluorescent tracers (FTs). Except for the methods of conjugation of different FTs to antibodies, other procedures including standard curves for making tests strips are the same between quantum dots and lanthanide chelates. Conjugation of quantum dots to antibodies was carried out using Quantum Dot Labeling Kit (Cat# Q0101, NajingTech, Hangzhou, China).

Example 1—SAM Quantitative Tests

Format 1: A Homogeneous Immunoassay for a Quick Quantification of SAM

Employ the homogeneous immunoassay such as Homogeneous Time-Resolved Fluorescence (HTRF® technology, as exemplified in our application Ser. No. 15/091,544 filed Apr. 5, 2016, the entire contents of which are incorporated by reference herein as if they were entirely denoted) and the competitive method to quantify SAM from samples by using anti-SAM monoclonal antibody and bio-conjugates (as exemplified in our application Ser. No. 15/091,544 filed Apr. 5, 2016, the entire contents of which are incorporated by reference herein as if they were entirely denoted.)

(1) Use of the Biotin, Digoxigenin or Digoxin Conjugated SAM or SAM Analogs as Well as d2-Conjugated SAM or SAM Analogs with Different Lengths of Linkers in the Methods Described in FIG. 8 on HTRF®

Rabbit anti-mouse IgG-XL665 and Europium (Eu3+) cryptate labeling kit were purchased from Cisbio Bioassays. Label mouse anti-digoxin or anti-digoxigenin antibody (anti-Dig antibody, PerkinElmer) to Eu3+ cryptate. Optimize the dosage of each of the following components: Digoxin(Digoxigenin)-6C-aza-SAM, anti-Digoxin(Digoxigenin)-antibody-Eu3+ cryptate, mouse-anti-SAM antibody 118-6 and rabbit anti-mouse IgG-XL665 in a buffer containing 100 mM PB, pH 7.0, 0.1% protease-free BSA, 100 mM KF, 0.1% Tween 20. In a competitive HTRF assay, SAM standard is used in the range of 0-3000 nM. The test is performed with a micro-titer strip of 1-10 wells to a final volume of 100 µl/well. All assay components are combined and incubated for about 30 min at room temperature. The assay plates are read with a small point-of-care micro-titer strip reader for HTRF assays. Time-resolved fluorescence is measured at a 50 µs delay after each excitation pulse. Emissions are measured at 665 nm for detection of the FRET signal (A counts), and at 620 nm for detection of the Eu(K) signal (B counts). The B counts should be the same for all assay wells, which act as an internal control and indicator of the absorbance of the background. The fluorescent signals are measured simultaneously, and the ratio ((A counts−10,000)/B counts) is reported. This ratio is minimally affected by absorbance as both the 665 nm and the 620 nm signals are impacted similarly. The ratio and the concentration of the SAM standards are used to plot the standard curve. The more the SAM is from a sample, the lower the A counts and hence the ratio.

(2) Use of the Luciferase-6C-Aza-SAM in BRET

Mouse anti-SAM antibody 118-6 was conjugated to Alexa Fluor 610-x using fluorescent antibody labeling kit (Thermo-Fisher). Optimize the molar ratio of the bio-conjugate to luciferase, molar ratio of mouse anti-SAM antibody to Alexa Fluor 610-x, the working concentrations of Luciferase-6C-aza-SAM (donor Luc-SAM), mouse anti-SAM antibody 118-6 (acceptor FL-Ab) and the competing SAM from a sample or standard in a buffer containing 100 mM PB, pH 7.0, 0.1% protease-free BSA, 100 mM KF, 0.1% Tween 20. In a competitive BRET assay, SAM standard is tested in the range of 0-3000 nM. The test is performed with a micro-titer strip of 1-10 wells to a final volume of 100 µl/well. Three assay components above and the substrate luciferase are combined and incubated for 15-30 min at room temperature. The assay plates are read with a small point-of-care micro-titer strip reader for BRET assays. Time-resolved fluorescence is measured at a 50 µs delay after each excitation pulse. Emissions are measured at 630 nm for detection of the BRET signal, and at 550 nm for detection of the luciferin signal. Find the proper molar ratio of The BRET index (FL-Ab/Luc-SAM). With the right Luc-SAM (molar ratio Luc:SAM as 1:20) and FL-Ab (molar ratio FL:Ab as 4-8:1) conjugates, the amount of antibody bound is in linear relationship with BRET index, the BRET index and the concentration of the SAM standards are used to plot the standard curve. The more the SAM is from a sample, the lower the BRET index.

Format 2: A Fluorescent Immunochromatographic Strip for a Quick Quantification of SAM (1) Conjugation of monoclonal antibody against SAM to fluorescent tracers and then applied the conjugate evenly to 33GLASS (GE Healthcare Biosciences Corp. Piscataway, N.J.): The uniform europium dyed microspheres (0.20 µm diameter polymer P(S/V-COOH), Bangs Laboratories. Inc. Fishers, Ind.) were washed twice with MES (2-N-morpholino ethanesulfonic acid) at 14,000 rpm centrifugation for 10 minutes. Added EDC (1-Ethyl-3-(3-dimethylaminopropyl)-carbodiimide) to 1.5 mg/ml, N-hydroxysuccinimide (NETS) to 2 mg/ml to activate the polymer. Added anti-SAM antibody 84-3 (Cat# MA00202, Arthus Biosystems, VA) at the final concentration of 40 µg/ml and shaken at room temperature for 2.5 h. The conjugate was stored in 20 mM Tris buffer with 0.5% BSA and EDTA-Na2, applied evenly to the glass fiber after proper dilution at the density of 4 ul/cm, followed by drying at 37° C. for 12 h.

(2) Immobilized BSA-SAM at 0.2 mg/ml for test line (T) and goat anti-mouse antibody for control line (C) at 1.2 mg/ml onto a nitrocellulose membrane: The reagents were immobilized with 50 mM phosphate buffer, pH 7.4. The membranes were dried at 56° C. overnight and then assembled with the sample pad and the adsorption membrane. The resulting multi-membrane composite was cut into 3.8-mm test strips. The test strips were packed in a specialized black PVC cassette and then placed to a sealed aluminum foil bag containing silica gel as a desiccant.

(3) Sample pad was processed with anti-RBC (red Blood Cell) antibody, Tween 20, BSA and EDTA-Na2 in 50 mM Tris buffer so that all blood sample types can be used. The composition of a test strip is illustrated in FIG. 1A.

Figure 2:
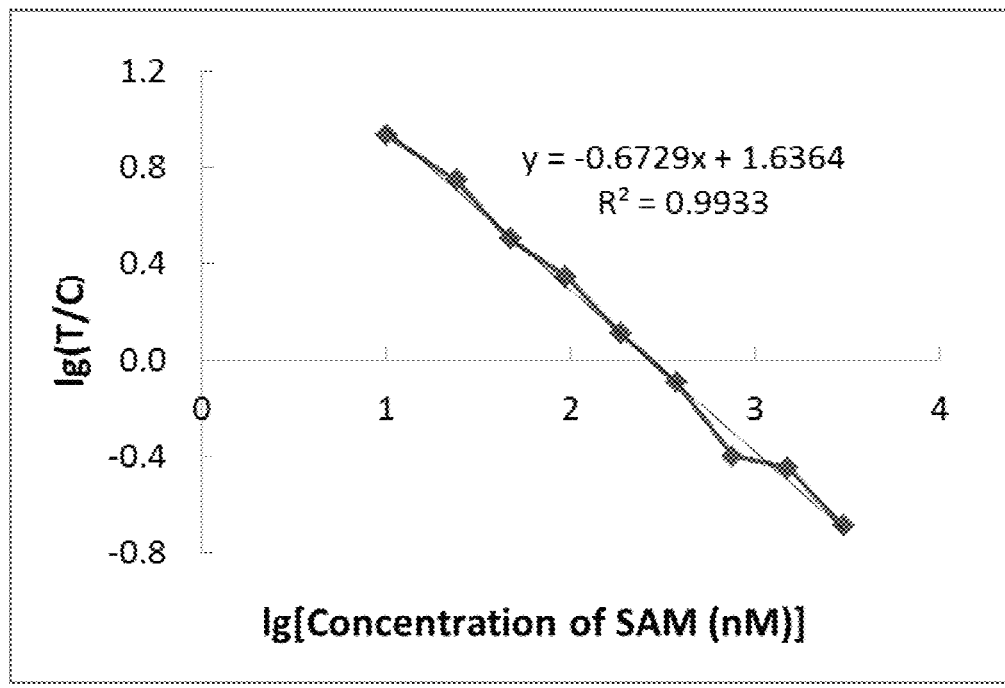
FIG. 2 shows the standard curve for the SAM fluorescent immunochromatographic test strip of example 1 invention.

(4) Measurement: About 100 µl of plasma or serum sample or 50 µl whole blood plus 50 µl dilution buffer was added to the sample well of the test strip cassette. In 15 minutes, insert the cassette into the slot of a fluorescence reader (with 365 nm excitation light). The fluorescence intensity was measured, which would be converted into actual levels of SAM based on the preinstalled standard curve (FIG. 2) calculated and updated per batch of strips. For this particular strip, the standard curve is shown in FIG. 2, where the x-axis is base 10 logarithm of the concentration of SAM ranging from 0 to 3000 nM. The y-axis is the base 10 logarithm of the ratio of fluorescent signal of test line (T) to that of control line (C).

Example 2—SAH Quantitative Tests

Format 1: A Homogeneous Immunoassay for a Quick Quantification of SAH

Employ the homogeneous immunoassay such as Homogeneous Time-Resolved Fluorescence (HTRF® technology, as exemplified in our application Ser. No. 15/091,544 filed Apr. 5, 2016, the entire contents of which are incorporated by reference herein as if they were entirely denoted) and the competitive method to quantify SAH from samples by using anti-SAH monoclonal antibody and bio-conjugates (as exemplified in our application Ser. No. 15/091,544 filed Apr. 5, 2016, the entire contents of which are incorporated by reference herein as if they were entirely denoted.). The uses of the biotin, digoxigenin or digoxin conjugated SAH, d2-conjugated SAH with different lengths of linkers in HTRF®, and luciferase conjugated SAH in BRET with different lengths of linkers in the methods described in the FIG. 8 are similar to the procedures describe in the Example 1 Format 1 in this invention except for using anti-SAH antibody and SAH when anti-SAM antibody and SAM (or SAM analogs) were used.

Figure 3:
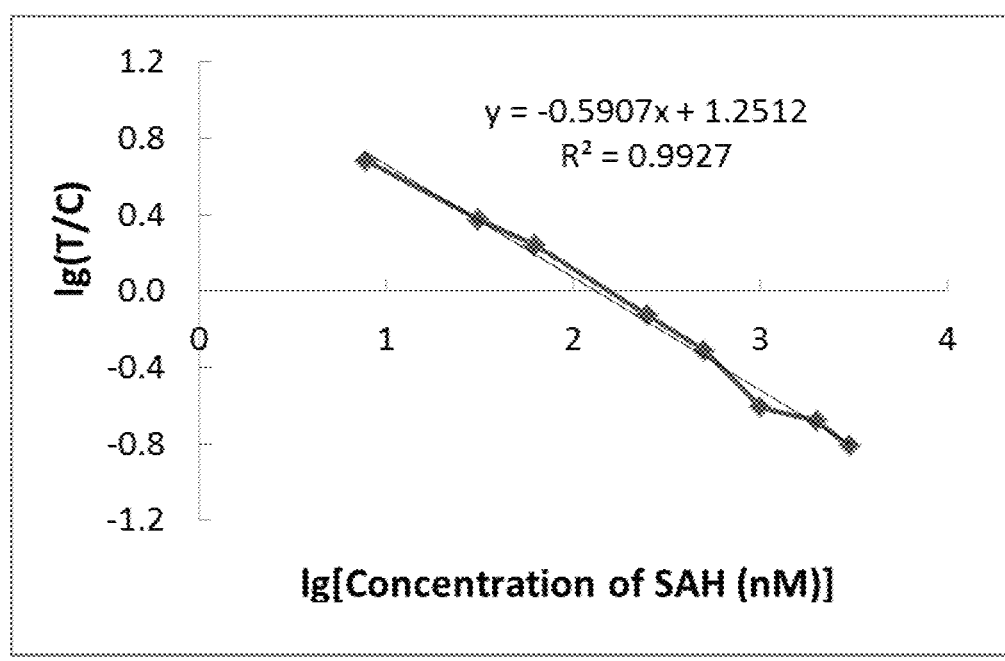
FIG. 3 shows the standard curve for the SAH fluorescent immunochromatographic test strip of example 2.

Format 2: A Fluorescent Immunochromatographic Strip for a Quick Quantification of SAH Used the same procedure as Example 1 above, a mouse anti-SAH antibody 301-3 derived from hybridoma clone 301-3 (A sample of the subject hybridoma clone 301-3 was deposited at the China Center For Type Culture Collection (CCTCC) Address: Wuhan University, Wuhan Zip code: 430072 on Sep. 15, 2014, and has been assumed the CCTCC number C2014178. (Cat# MA00303, Arthus Biosystems, VA) was used at the final concentration of 80 µg/ml. The standard curve for this particular strip is shown in FIG. 3, where x-axis is base 10 logarithm of the concentration of SAH ranging from 0 to 3000 nM. The y-axis is the base 10 logarithm of the ratio of fluorescent signal of test line (T) to that of control line (C).

Example 3—MI Strip

A Fluorescent Immunochromatographic Test Strip for Measuring Methylation Index (MI)

Using the method of Example 1 as described above but BSA-SAM (or SAM analog) and BSA-SAH were applied to different areas of the NC membrane and dried. Both FT-anti-SAM and FT-anti-SAH were absorbed evenly to the glass fiber, and then assembled as shown in the FIG. 1B. The fluorescence intensity of the FT was measured separately, which will be converted into actual levels of SAM and SAH based on the preinstalled standard curves for the batch of strips. SAM and SAH test lines will display as two same or different colors depending the type of FTs used to label the anti-SAM and anti-SAH antibodies. The strip allows measuring SAM and SAH at the same time quickly and easily. MI is calculated and displayed on the Dry Immunofluorescence Analyzer.

Example 4—CRP Quantitative Strip

A Fluorescent Immunochromatographic Strip for a Quick Quantification of Full CRP (1) Conjugation of monoclonal antibody against CRP to fluorescent tracers and then applied the conjugate evenly to 33GLASS (GE Healthcare Biosciences Corp. Piscataway, N.J.): The uniform europium dyed microspheres (0.20 µm diameter polymer P(S/V-COOH), Bangs Laboratories. Inc. Fishers, Ind.) were washed twice with MES (2-N-morpholino ethanesulfonic acid) and separated at 14,000 rpm centrifugation for 10 minutes. Added EDC (1-Ethyl-3-(3-dimethylaminopropyl)-carbodiimide) to final concentration of 1.5 mg/ml, N-hydroxysuccinimide (NETS) to 2 mg/ml to activate the polymer. After washing with MES, microspheres was reconstituted in 500 µl MES pH 6.0. Added anti-CRP antibody M-5191 (Biobridge, Beijing, China) 7 µl (2.82 mg/ml) and shaken at room temperature for 2.5 h. The conjugate was stored in 20 mM Tris buffer with 0.5% BSA and EDTA-Na$_2$, applied evenly to the glass fiber after 1:3 dilution at the density of 4 ul/cm, followed by drying at 37° C. for 18 h.

(2) Immobilized anti-CRP antibody M-5192 (Biobridge, Beijing, China) at 0.05 mg/ml for the first test line (T1) and 0.4 mg/ml for the second test line (T2), goat anti-mouse antibody for control line (C) at 1.2 mg/ml onto a nitrocellulose membrane: The reagents were immobilized with 50 mM phosphate buffer, pH 7.4. The membranes were dried at 56° C. overnight and then assembled with the sample pad and the adsorption paper. The resulting multi-membrane composite was cut into 3.8-mm test strips. The test strips were packed in a specialized black PVC cassette and then placed to a sealed aluminum foil bag containing silica gel as a desiccant.

(3) The composition of the test strip is illustrated in FIG. 1B without a sample pad as blood samples will be diluted at about 600 folds before testing.

(4) Measurement: About 100 µl of diluted plasma or serum sample or whole blood plus was added to the sample well of the test strip cassette. In 15 minutes, insert the cassette into the slot of a fluorescence reader (with 365 nm excitation light). The fluorescence intensity was measured, which would be converted into actual levels of CRP based on the preinstalled standard curve (FIG. 4) calculated and updated per batch of strips.

Figure 4:
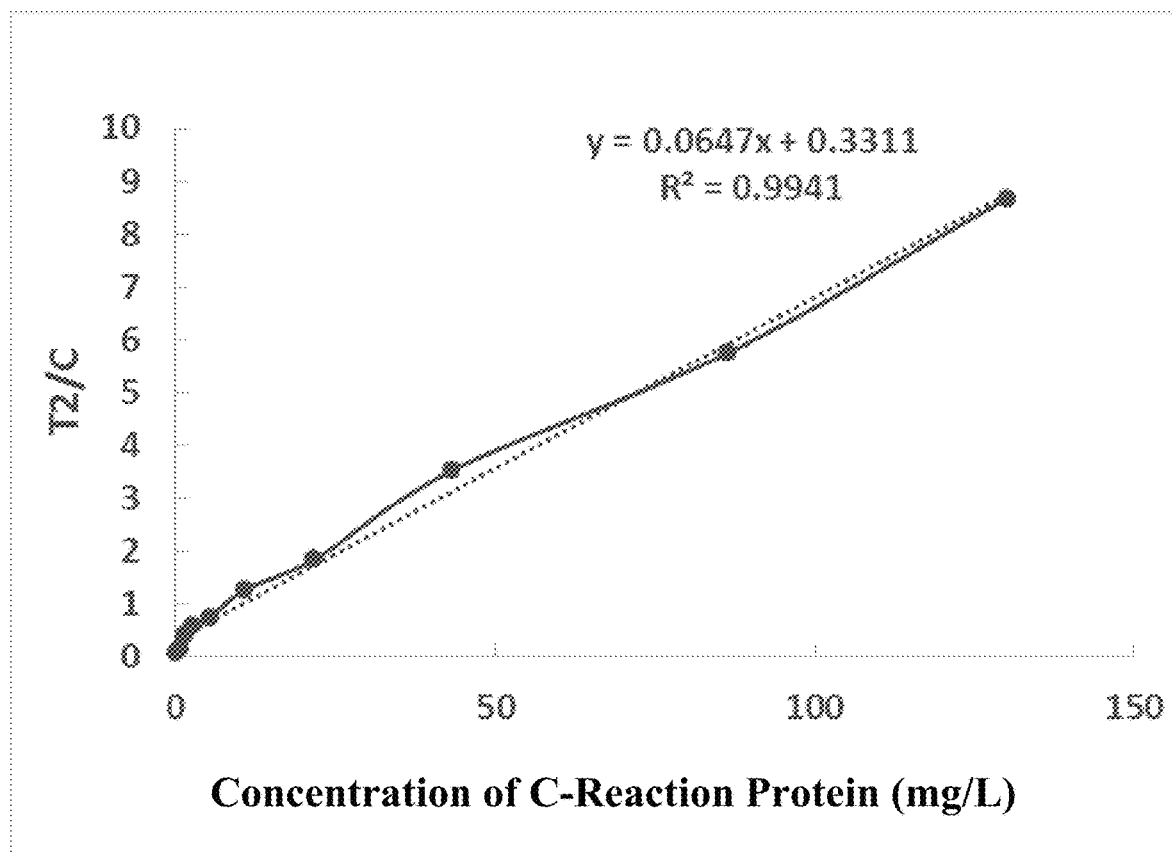
FIG. 4 shows the standard curve for a CRP fluorescent immunochromatographic strip of example 4.

The standard curve for this particular strip is shown in FIG. 4, where the x-axis is the concentration of CRP ranging from 0 to 130 mg/L. The y-axis is the ratio of fluorescent signal of the second test line (T2) to that of control line (C).

Example 5—HCy Quantitative Tests

Format 1: A Homogeneous Immunoassay for a Quick Quantification of HCy

Employ the homogeneous immunoassay such as Homogeneous Time-Resolved Fluorescence (HTRF® technology, as exemplified in our application Ser. No. 15/091,544 filed Apr. 5, 2016, the entire contents of which are incorporated by reference herein as if they were entirely denoted) and the competitive method to quantify HCy from samples either by using anti-HCy monoclonal antibody or by measuring the level of SAH that is generated from the biochemical reaction describe in the Example 6. The method to measure SAH is the same as the procedure descried in the Example 2 Format 1.

The uses of the biotin, digoxigenin or digoxin conjugated HCy, d2-conjugated HCy with different lengths of linkers in HTRF®, and luciferase conjugated HCy in BRET with different lengths of linkers in the methods described in the FIG. 8 are similar to the procedures describe in the Example 1 Format 1 in this invention except for using anti-HCy antibody and HCy when anti-SAM antibody and SAM (or SAM analogs) were used.

Format 2: A Fluorescent Immunochromatographic Strip for a Quick Quantification of HCy Employ the similar method as in the Example 1 Format 2 to quantify HCy from samples either by using anti-HCy monoclonal antibody or by measuring the level of SAH that is generated from the biochemical reaction describe in the Example 6.

Example 6—HCy Qualitative Strip

An Immunochromatographic Test Strip for a Quick Qualitative Measurement of HCy

Materials:

| Reagent | Stock Solution | Reagent | Stock Solution |
|---|---|---|---|
| DTT | 100 mM | Boric acid buffer | 0.2M pH 8.2 |
| SAH-Na | 100 uM | Tris buffer | 0.1M pH 8.2 |
| HMT | 0.2 mg/ml in 30% glycerol | PBS | 0.1M pH 7.4 |
| SAM | 100 uM | $K_2CO_3$ | 0.2M |
| Homocysteine | 100 uM | D-Trehalose | 30% |
| Goat-anti-mouse IgG | 7.8 mg/ml | sucrose | 50% |
| Anti-SAH antibody | 5.1 mg/ml | BSA | 10% |
| SAH-BSA | 3.73 mg/ml | colloidal gold | 70 nm in diameter |

Other materials include glass fiber K88 (Tongcheng Paper Production, Co, Ltd, Anhui, China), nitrocellulose membrane, Trion X-100, Tween 20, casein, fetal bovine serum and PVP (Polyvinylpyrrolidone). Mouse anti-SAH antibody (Cat # MA00307, Arthus Biosystems, VA).

HCy plasma or serum samples underwent some chemical reactions so that all HCys were freed from protein associations and in a reductive form before they were converted to SAH as follows:

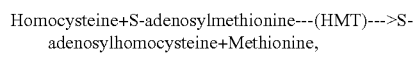

Homocysteine+S-adenosylmethionine---(HMT)--->S-adenosylhomocysteine+Methionine, whereas HMT is homocysteine methyltransferase. Test reaction: 3 µl HCy, 3 µl SAM, 3 µl HMT and 91 ul 100 mM PBS, pH7.4; control reaction: 41 HCy, 3 µl SAM, 30% glycerol and 91 ul 100 mM PBS, pH7.4. Thoroughly mixed and let it react for 5 min and then added 80 µl to SAH test strip.

The reaction product SAH is measured with a qualitative SAH strip with a proper cutoff value that reflects the cutoff value of limiting material HCy in human plasma or serum, i.e. normal subjects have HCy at 10 µM and below; patients with abnormal HCy that is higher than 15 µM. Therefore, we made a colloidal gold SAH test strip that shows test line (T) and control line (C) with the following readout:

C line does not have any colloidal gold signal: the strip is invalid.

Both T and C have the similar colloidal gold signal intensity: HCy level from a sample <10 µM;

The C has much stronger colloidal gold signal than T line and T line is barely visible: HCy level from a sample >=15 µM;

The C has stronger colloidal gold signal than T line and T line is visible: HCy level from a sample is between 10 to 15 µM;

The SAH test strip was made according to the following procedure:

(1) 1 ml 70 nm colloidal gold, 27 µl $K_2CO_3$, 8 µl mouse anti-SAH antibody, rested for 20 min, then added 100 µl 10% BSA, rested for 15 min followed by centrifuging at 12,000 rpm for 15 min. Discarded supernatant. Washed with 20 mM boric buffer containing 1% BSA, D-Trehalose and sucrose once, and reconstituted in 120 µl boric buffer.

(2) Applied the conjugated antibody at 4 µl/cm to glass fiber K88 evenly.

(3) Sample pad was processed with 100 mM Tris pH 8.2 containing 0.1-2% PVP, Triton x-100 and casein. Dried at 37° C. overnight.

(4) Test strip was assembled on a PVC plate according to the method illustrated in the FIG. 1A.

Example 7—MIHC Strip

An Immunochromatographic Test Strip for Simultaneous Measurement of SAM, SAH and HCy MIHC1 represents a methylation index and homocysteine triple test strip format 1. The unit consists of two test strips. (a) One is an MI strip as in Example 3. (b) The other one is an HCy strip as in Example 5.

MIHC2 represents a methylation index and homocysteine triple test strip format 2. The unit consists of two test strips. (a) One is an MI strip as in Example 3. (b) The other one is an HCy strip as in Example 6.

The accompanying device is able to read, process and output the results at the same time reporting the values of SAM, SAH, MI and HCy from a sample qualitatively or/and quantitatively.

Example 8—MIHCR Strip

An Immunochromatographic Strip for Simultaneous Measurement of SAM, SAH, Homocysteine (HCy) and CRP MIHCR1 represents a methylation index, homocysteine and C-reactive protein quadruple test strip format 1. The unit consists of three test strips. (a) One is an MI strip as in Example 3. (b) The second one is an HCy strip as in Example 5. (c) The third one is the CRP strip as in Example 4.

MIHCR2 represents a methylation index, homocysteine and C-reactive protein quadruple test strip format 2. The unit consists of three test strips. (a) One is an MI strip as in the Example 3. (b) The second one is an HCy strip as in Example 6. (c) The third one is the CRP strip as in Example 4.

The accompanying device is able to read, process and output the results at the SAM time reporting the values of SAM, SAH, MI, CRP and HCy from a sample qualitatively or/and quantitatively.

Example 9—SAM Semi-Quantitative Strip

Colloidal Gold or Colloidal Microsphere Semi-Quantitative Test Strip for SAM

The test unit does not require any device to read results. Triple test strips are assembled into one single unit with each strip having detection band at cutoff values of 50 nM, 400 nM, 800 nM respectively. The cutoff values can be changed to different values besides 50 nM, 400 nM and 800 nM. The value from a blood sample can be read out as the following: <50 nM; 50-400 nM; 400-800 nM; >800 nM. Colloidal gold or microspheres were used to label mouse anti-SAM antibody (Cat# MA00201, Arthus Biosystems, VA). Conjugation of antibody was similar to that in Example 6. Assembling of the test strip is the SAM as in shown FIGS. 1A and in the Example 1. Colloidal gold or microsphere results can be seen with naked eyes. Therefore, this method is quick, easy and cost-effective without having to use any additional device.

Example 10—SAH Semi-Quantitative Strip

Colloidal Gold or Colloidal Microsphere Semi-Quantitative Test Strip for SAH The test unit does not require any device to read results. Triple test strips are assembled into one single unit with each strip having a detection band with cutoff values of 200 nM, 600 nM, 1200 nM respectively. The cutoff values can be changed to different values besides 200 nM, 600 nM and 1200 nM. The value from a blood sample can be read out as the following: <200 nM; 200-600 nM; 600-1200 nM; >1200 nM. Colloidal gold or microspheres were used to label mouse anti-SAH antibody 839-6 (Cat# MA00307, Arthus Biosystems, VA). Conjugation of antibody was similar to that in Example 6. Assembling of the test strip is the SAM as in shown FIG. 1A and in the Example 1. Colloidal gold or microsphere results can be seen with naked eyes. Therefore, this method is quick, easy and cost-effective without having to use any additional device.

Example 11—Other Immunoassay Systems

Besides using dry test strip format as described above, FTs can also be used in other aqueous systems as tracers in a list of potential measurements below.

FT-anti-SAM and FT-anti-SAH antibodies can be used in cell-base technologies such as flow cytometry and immunofluorescence microscopy to investigate the metabolism, dynamics, distribution and levels of SAM and SAH within cells, tissues and organs under different scenarios.

A. FCM (Flow Cytometry)

Figure 5:
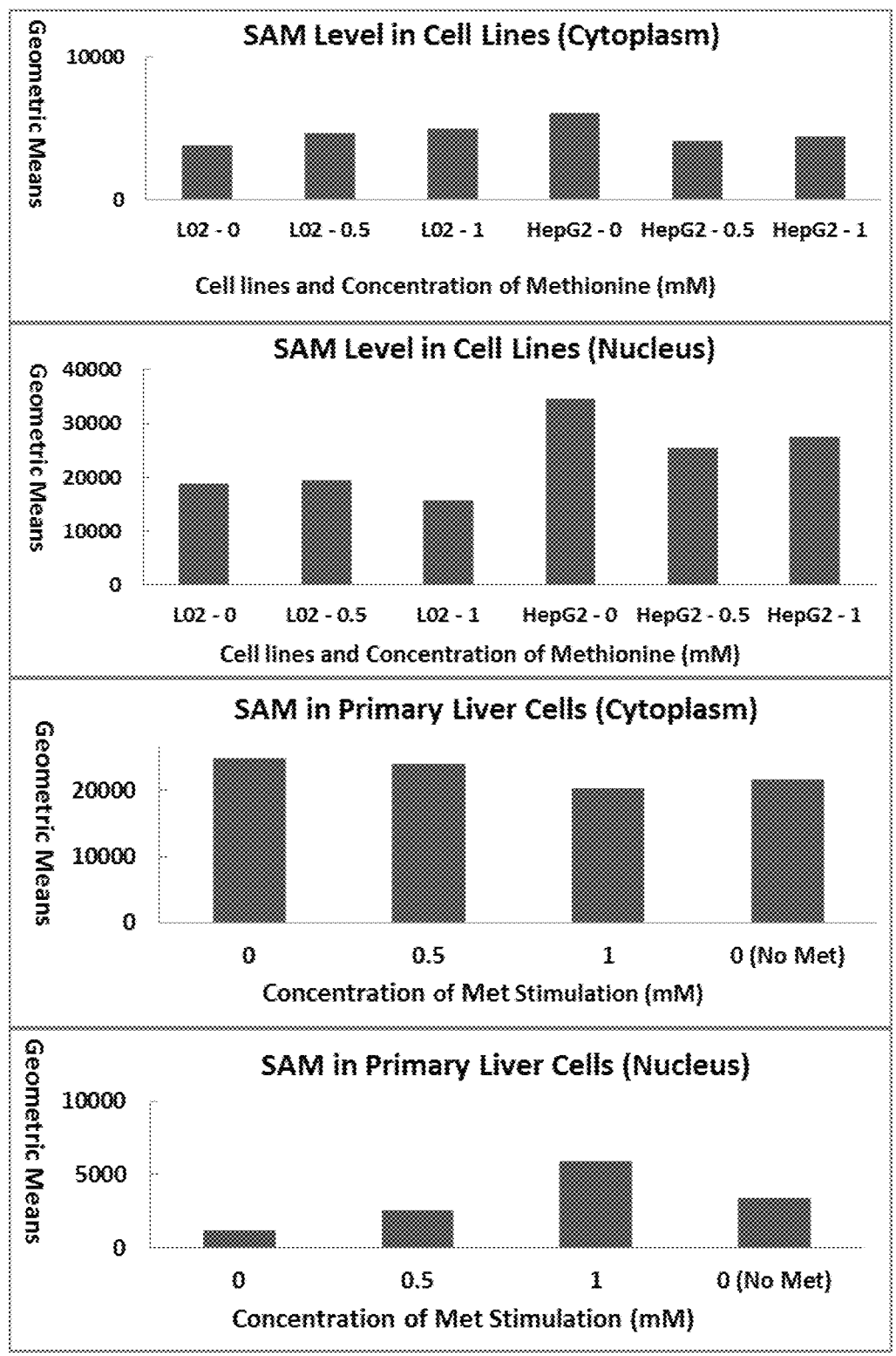
FIG. 5 illustrates the flow cytometry (FCM) results from cells double stained with Alexa Fluor 647 conjugated anti-SAM 118-6 antibody (Cat# MAF00201, Arthus Biosystems, VA) at 4.5 µg/ml.
Figure 6:
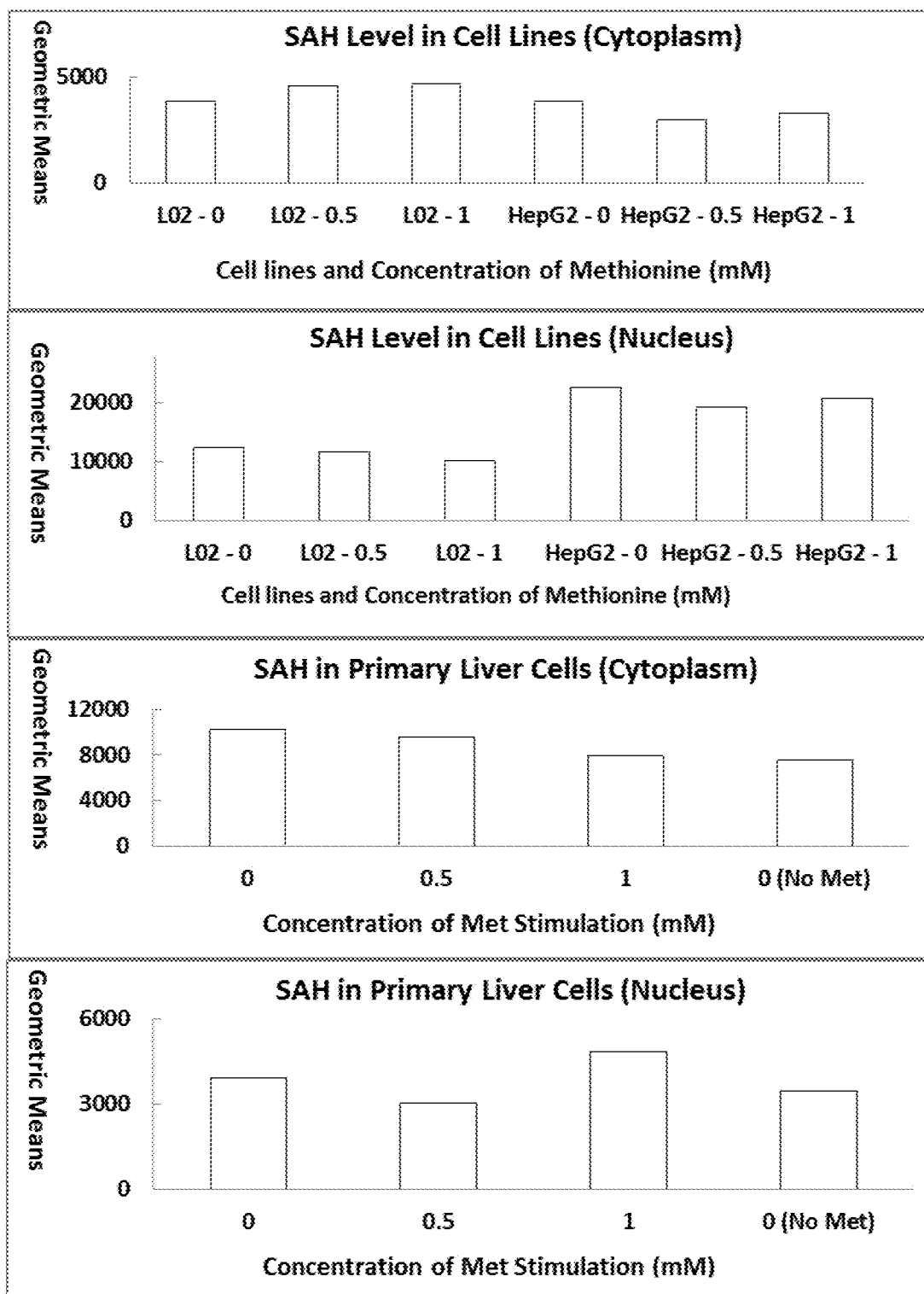
FIG. 6 shows FCM results from cells double stained with Alexa Fluor 488 conjugated anti-SAH antibody 301-3 derived from hybridoma clone 301-3 (Cat# MAF00301, Arthus Biosystems, VA) at 45 µg/ml. A sample of the subject hybridoma clone 301-3 was deposited at the China Center For Type Culture (CCTCC) Address: Wuhan University, Wuhan Zip code: 430072 on Sep. 15, 2014. and has been assigned the CCTCC number C2014178.

MAT activity was stimulated by Met in cells using FCM. SAM and SAH were double stained and analyzed from cells after cultured and treated as indicated in FIG. 5. The FCM results are consistent with the results form ELISA (data not shown) and LSCM yet FCM provides more information about changes of SAM levels in nucleus and cytoplasm compartments. The effects of Met-stimulated MAT activities have similar pattern for cytoplasm and nucleus, which is different from the effects on primary liver cells. Higher dosage of Met (1 mM) inhibits instead of stimulates (as in 0.5 mM Met) MAT activity in L02 cells in nuclei whereas 1 mM Met continuously stimulates MAT activity in cytoplasm of L02 cells. Met inhibits MAT activity in HepG2 both in cytoplasm and nucleus and thus SAM is decreased (FIG. 5A). In both cell lines, nuclear SAM constitutes 80-85% of the total SAM and methylation indices are similar too. In normal mouse liver cells, about 4.6% of SAM is located in nucleus. With 1 mM Met-stimulation for 24 h, nuclear SAM level is increased by 4 folds, constitutes about 22.5% of the total SAM. Met-stimulated MAT causes nuclear SAM to increase whereas cytoplasm SAM is decreased within 1 mM Met dosage. Primary liver cells were cultured in Met-free medium for 20 h, MAT activity was induced and SAM was increased in nucleus but was reduced in cytoplasm (FIG. 6). This indicated critical roles that SAM needs to play are in nucleus in response to Met hunger/deficiency (regulated expressions of certain genes). In the current test conditions, cytoplasm and total cell methylation index (MI) was 1.85-2.55, but the MI was 0.3 in normal liver nucleus that was increased to 1.2 after stimulation with 1 mM Met. Nuclear MI was 0.98 in Met-free medium cultured for 20 h, which is about 3-fold higher than normal liver cells and is consistent with the changes of SAM levels.

Two different types of fixation/permeabilization buffers were tested for all cell types, i.e. nuclear fixation/permeabilization buffer (Cat#00-5523 FoxP3_TF Staining Buffer Set, eBioscience, San Diego, Calif.) by which both cytoplasm and nucleus targets were stained and intracellular fixation/permeabilization buffer was used (Cat#00-8824, eBioscience, San Diego, Calif.) by which only cytoplasm targets were measured.

(1) Prepare cell suspension according to the protocol of cell digestion with trypsin;

(2) Centrifuge cell suspension at 1500 rpm for 5 minutes and abandon the supernatant;

(3) Re-suspend the cells with at least 1 ml PBS in about 106 cells/sample;

(4) Centrifuge at 1500 rpm for 5 minutes and abandon the supernatant;

(5) Add 100 µl fixation buffer to each sample (if the fixation buffer was 4% paraformaldehyde, add 400 µl/sample). Keep the samples in dark at room temperature for 30 minutes, and then centrifuge the suspension at 1500 rpm for 5 minutes and abandon the supernatant;

(6) Wash with 100 µl permeabilization buffer and then centrifuge the suspension and abandon the supernatant;

(7) Incubate with 100 µl permeabilization buffer at room temperature for 20 minutes, and then centrifuge the suspension and abandon the supernatant;

(8) Re-suspend with 100 µl permeabilization buffer. Add 10 µl fluorescence labeled antibodies and incubate it for 30 minutes.

(9) Wash with PBS for twice and re-suspend the cells in 0.5 ml PBS for measurements with BD FACSCanto II Flow Cytometer. The results are shown in FIGS. 5 and 6.

FIG. 5 shows the flow cytometry (FCM) results from cells double stained with Alexa Fluor 647 conjugated anti-SAM 118-6 antibody (Cat# MAF00201, Arthus Biosystems, VA) at 4.5 µg/ml while FIG. 6 shows FCM results from cells double stained with Alexa Fluor 488 conjugated anti-SAH antibody 301-3 derived from hybridoma clone 301-3 (A sample of the subject hybridoma clone 301-3 was deposited at the China Center For Type Culture Collection (CCTCC) Address: Wuhan University, Wuhan Zip code: 430072 on Sep. 15, 2014, and has been assigned the CCTCC number C2014178). (Cat# MAF00301, Arthus Biosystems, VA) at 45 µg/ml. Both SAM and SAH levels from cytoplasm and nucleus compartments are shown. Normal liver cell line L02 and hepatocellular carcinoma cell line HepG2 were treated with 0, 0.5 mM and 1 mM methionine (Met) for 24 h. Mouse primary liver cells were isolated and treated with 0, 0.5 mM, 1 mM Met for 24 h and cultured in Met-free MEM medium for 20 h. FIG. 5 shows SAM levels while FIG. 6 shows SAH levels.

B. Immunofluorescence Laser Scanning Confocal Microscopy (LSCM)

(1) Cleaned with alcohol the special pieces of glasses for LSCM (that are designed to allow cells to grow on easily and be taken photos under microscope). Placed under UV light in the hood for at least 10 minutes.

(2) Put the glasses into 24-well cell culture plate using sterile tweezers. Seed proper amount of cells (normal liver cell line L02 and hepatocellular carcinoma cell line HepG2) based on the knowledge of cell growth rate (e.g. 5×104/well). Culture for 24 h with or without any tests designed, e.g. methionine stimulation.

(3) When cells were ready to be stained, removed medium from wells and washed with 1 ml 1×PBS for 3 times.

(4) Added 200 µl 80%–20° C. stored acetone to fix the cells under –20° C. for 30 minutes.

(5) Wash with 1 ml 1×PBS for 3 times.

(6) Added Alexa Fluor-488-anti-SAH antibody at 40 μg/ml and Alexa Fluor 647-anti-SAM antibody at 8 μg/ml in 200 μl staining buffer (PBS with 1% BSA). Put the plate under 4° C. for 1 h. Add proper amount of DAPI for 5 minutes to stain nuclei only.

(7) Washed with 1 ml 1×PBS for 3 times.

(8) Sealed the glass with the special resin that is especially designed to be used for LSCM to prevent fluorescence from being quenched.

(9) Observed and took photos with Zeiss LSM 780 with 630-fold magnification. The results are shown in FIG. 7 which illustrates the Laser Scan Confocal Microscopy (LSCM) results of L02 and HepG2 cells that were cultured for 40 h and then stained with the same fluorescence labelled anti-SAM and anti-SAH antibodies of the invention. In FIG. 7, A are the L02 cells stained with anti-SAM antibody; B are the HepG2 cells stained with anti-SAM antibody; C are L02 cells stained with anti-SAH antibody; and D are HepG2 cells stained with anti-SAH antibody. The photos were taken by Zeiss LSM 780 under 630-fold magnification.

C. Fluorescence Immunology in Connection with Streptavidin (SA) and Biotin System Instead of directly or indirectly labeling FTs to anti-SAM and anti-SAH antibodies, different sizes or colored quantum dots can be labeled onto SA. (1) SAM and SAH are conjugated with biotin through various linkers (as exemplified in our application Ser. No. 15/091,544 filed Apr. 5, 2016, the entire contents of which are incorporated by reference herein as if they were entirely denoted). (2) Different FTs are labeled onto SA. (3) Through the specific and strong binding between SA and biotin, small molecule antigen SAM and SAH can be therefore labeled to different FTs separately, i.e. FT-SAM and FT-SAH are obtained. (4) If wishing to measure SAM and SAH simultaneously in a sample, mix the different colored FT-SAM and FT-SAH and use competitive mechanism in an immunoassay to quantify SAM and SAH with the use of specific antibodies against SAM and SAH.

D. Fluorescence Immunology in Connection with Digoxingenin—Anti-Digoxingenin Antibody System Other indirect methods of tracing SAM and SAH include (1) conjugating SAM or/and SAH to digoxigen or digoxingenin through various linkers (as exemplified in our provisional application Ser. No. 15/091,544 filed Apr. 5, 2016, the entire contents of which are incorporated by reference herein as if they were entirely denoted). (2) Different FTs are labeled onto mouse anti-digoxigenin or mouse anti-digoxin antibodies. (3) Mix products from step (1) and step (2), so SAM and SAH are indirectly labeled to different colored FTs. (4) Uses of FT-SAM and FT-SAH are as described above as in Example 11C.

Example 12—Using the Test Strips to Measure SAM and SAH Levels from Healthy Human Blood Samples and Monitoring Progress in Weight Reduction About 5 ml blood samples were drawn via I.V. into heparinized tubes from 34 healthy subjects (volunteers from our R&D department, subjects were fasting for at least 5 hours). 100 μl plasma samples were added to the SAM and SAH immunochromatographic test strips as described in the Example 1 and 2 above and the values were read from Dry Immunofluorescence Analyzer Model FIC-S2011 series (Arthus Biosystems, VA). As can be seen from the Table 1, the averages of SAM, SAH and MI from 15 females were higher than (SAM 25.51%, SAH 74.25%, MI 19.15% higher respectively) those corresponding values from 18 male subjects.

TABLE 1

Levels of SAM, SAH and MI in healthy plasma samples by gender

|  | BMI | SAM (nM) | SAH (nM) | MI | Gender | Case |
| --- | --- | --- | --- | --- | --- | --- |
| AVG. | 22.00 | 256.80 | 86.60 | 5.60 | F | 15 |
| STDEV. | 3.93 | 164.24 | 37.95 | 4.45 | F | 15 |
| AVG. | 22.60 | 204.60 | 49.70 | 4.70 | M | 18 |
| STDEV. | 2.20 | 103.85 | 32.37 | 2.318 | M | 18 |

We further separated groups based on BMI (Body Mass Index) within each gender group. BMI information was missing for one of the male subjects. The averages of SAM, SAH and MI and the standard deviations were shown in Table 2. The averages of SAM and MI in high BMI (BMI>24) groups were obviously decreased as compared to those in low BMI (BMI<=24) groups for both female and male subjects. With average SAM at 143.7 nM from high BMI group versus SAM at 285.07 nM from low BMI group in females, and average SAM at 185 nM from high BMI group versus SAM at 214 nM from low BMI group in males. The average MI from the high BMI group is only 30.76% of the MI from the low BMI group in females and about 63.49% in male subjects. This implied that high BMI had more impacts on (reduced) MIs of females than on males. BMI less than 24 is considered ideal for health reason. Therefore, abnormal BMI is related to SAM levels in both genders. Low SAM might be the reason for the abnormal and unfavorable BMI that usually underlies a series of health concerns including cardiovascular and renal diseases, diabetes, obesity and other metabolic disorders, etc. (Lydi M. J. W. van Driel reported the relationship between BMI and methylation in young females (Body Mass Index Is an Important Determinant of Methylation Biomarkers in Women of Reproductive Ages, J. Nutr. 139: 2315-2321, 2009.). The results indicated SAM, SAH and MI are good indicators or biomarkers for health issues caused by abnormal BMI, such as cardiovascular diseases.

TABLE 2

Levels of SAM, SAH and MI in healthy plasma samples by gender and BMI

| | | | BMI >= 24 | | | | BMI < 24 | | |
|---|---|---|---|---|---|---|---|---|---|
| | Gender | Case | SAM(nM) | SAH(nM) | MI | Case | SAM(nM) | SAH(nM) | MI |
| AVG. | F | 3 | 143.70 | 85.05 | 2.0 | 12 | 285.06 | 86.96 | 6.5 |
| STDEV. | F | 3 | 88.46 | 27.42 | 1.9 | 12 | 168.97 | 102.43 | 4.4 |
| AVG. | M | 4 | 185.00 | 69.00 | 4.0 | 13 | 214.00 | 48.58 | 6.3 |
| STDEV. | M | 4 | 76.61 | 52.27 | 2.1 | 13 | 116.06 | 30.41 | 4.6 |

As BMI greater than 24 may indicate unhealthy conditions, we removed 3 female and 4 male cases with BMI higher than 24, Table 1 becomes Table 3 below. The averages of SAM, SAH and MI from 12 normal BMI females were higher than (SAM 33.41%, SAH 97.73%, MI 25% higher respectively) those corresponding values from 13 male subjects. Furthermore, by removing abnormal BMI cases, the differences of SAM, SAH and MI values between females and males were even more obvious, i.e. the average female SAM level is 33.41% (instead of 25.51% if subjects with all BMI values were considered) higher than that of male if only looking at the normal BMI subjects in each gender. Table 4 showed abnormal BMI may blur (decrease) the differences in SAM, SAH and MI values between females and males. This indicates BMI is a factor that complicates the values of SAM, SAH and MI, which is consistent with the fact that the levels of SAM and SAH vary according to race, gender, body weight, age and general healthy conditions.

TABLE 3

Levels of SAM, SAH and MI in healthy plasma samples by gender (all BMI < 24)

| | BMI | SAM (nM) | SAH (nM) | MI | Gender | Case |
|---|---|---|---|---|---|---|
| AVG. | 20.4 | 285.10 | 87.00 | 6.50 | F | 12 |
| STDEV | 2.17 | 168.97 | 102.43 | 4.48 | F | 12 |
| AVG. | 21.70 | 213.70 | 44.00 | 5.20 | M | 13 |
| STDEV | 1.60 | 116.06 | 25.40 | 2.41 | M | 13 |

TABLE 4

Percent increases of SAM, SAH and MI in females than males

| Group | SAM | SAH | MI |
|---|---|---|---|
| With all BMI | 25.51 | 74.25 | 19.15 |
| With healthy BMI (<=24) | 33.41 | 97.73 | 25.00 |

The correlation between BMI and MI levels and SAM levels appears to indicate that monitoring these biomarkers together with the BMI provide practical information in designing diets for a given set of a patient population.

Example 13—Using the Test Strips to Measure SAH, HCy, CRP and cTnI from Healthy and Cardiovascular Blood Samples The abbreviations used in this example are as follows: cTnI (Cardiac Troponin-I), CRP, CK-MB (Creatine-kinase-MB) and Myo (Myoglobin), The 9 healthy and 7 cardiovascular disease (CVD) human blood samples were obtained from patients diagnosed as cardio attacks in the clinical lab of The Second Affiliated Hospital of Xiangya Medical School, Central South University in Changsha, Hunan province. The samples were used to measure SAM, SAH, MI and CRP using the test strips from the Examples 1, 2, 3 and 4 in this invention. The data from Table 5 showed 9 cases without acute myocardial injury (AMI) as determined by clinical lab's negative cTnI, CRP, CK-MB and Myo results had the average SAM value as 164 nM, SAH as 232 nM, MI as 1.75 and 44.44% of them with HCy higher than 15 μM, and CRP values measured using test strip as described in the Example 4 showed an average of 0.8 mg/ml (normal). Whereas, in the 7 heart attack cases that were diagnosed with much increased cTnI, CRP, CK-MB and Myo the average SAM value was 94 nM, SAH as 558 nM, MI as 0.2 and 85.71% of them with HCy higher than 15 μM. The average CRP for the 7 cases with heart attack or AMI is 4.37 mg/l, which was higher than normal but not related to inflammation reaction as it is less than 10 mg/l. For the last two samples with higher Myo (increased in the first few hours of AMI), CRP levels were not high and just about to increase. For the first two cases with peak cTnI that normal occurs around 36 h post-AMI, CRP levels were much elevated. This indicated that CRP elevation happened after about a day or so. The results indicated that decreased SAM and MI, increased SAH and HCy are also good biomarkers for heart diseases. Only 1 of the 7 AMI patients showed negative HCy, yet the SAH level of this patient was extremely higher than other cases, about 5-fold higher than normal average SAH level. This indicated that SAH, MI are better indicators than HCy in diagnosing heart diseases.

The SAM, SAH, HCy and CRP values measured for all samples using the immunochromatographic test strips described in the Example 4 in this invention may help identify and sort out certain groups of patients that may be overlooked by merely checking cTnI, CK-MB, Myo and HCy alone with photochemical methods that are currently often checked. SAM, SAH, HCy and CRP are useful biomarkers that will add to the current cardiac panel in order to timely diagnose, differentiate, predict the prognosis and help direct treatment of CVDs.

TABLE 5

| Measurement of biomarkers in clinical samples (n = 16) | | | | | | | |
|---|---|---|---|---|---|---|---|
| Marker(ng/ml) | Value | CVD | SAM (nM) | SAH (nM) | MI | CRP (mg/l) | HCy |
| cTnI | 0.035 | − | 367 | 40 | 9.12 | 0.30 | − |
| cTnI | 0.22 | − | 48 | 50 | 0.95 | 0.31 | + |
| cTnI | 0.239 | − | 666 | 207 | 3.21 | 0.58 | − |
| CRP | 1.26 | − | 35 | 129 | 0.27 | 1.21 | + |
| CRP | 1.51 | − | 83 | 522 | 0.16 | 1.49 | − |
| CK-MB | 18.92 | − | 26 | 303 | 0.09 | 1.14 | − |
| Myo | 54.98 | − | 48 | 273 | 0.18 | 0.77 | − |
| Myo | 33.93 | − | 45 | 466 | 0.10 | 0.48 | + |
| Myo | 67.88 | − | 160 | 95 | 1.68 | 0.92 | + |
|  |  | AVG. | 164 | 232 | 1.75 | 0.80 |  |
|  |  | STDEV. | 217 | 175 | 2.95 | 0.42 |  |
| cTnI | >50 | + | 72 | 405 | 0.18 | 5.75 | + |
| cTnI | 45.6 | + | 211 | 1320 | 0.16 | 5.21 | − |
| CRP | 7.73 | + | 33 | 521 | 0.06 | 7.02 | + |
| CK-MB | 54.95 | + | 48 | 98 | 0.49 | 4.51 | + |
| CK-MB | 33.93 | + | 85 | 456 | 0.19 | 3.33 | + |
| Myo | 119.39 | + | 138 | 610 | 0.23 | 1.24 | + |
| Myo | 152.47 | + | 73 | 709 | 0.10 | 3.52 | + |
|  |  | AVG | 94 | 588 | 0.20 | 4.37 |  |
|  |  | STDEV. | 61 | 376 | 0.14 | 1.88 |  |

Based on experiments that have been conducted, as set forth in some of the preceding examples, it is believed that quantum dot probes and fluorescent chelates provide higher fluorescence than that provided by other probes that have been labeled with organic fluorescent molecules; and their longer lasting fluorescence allow for stable and reliable systems to be built; Therefore, it is believed that quantum dot and fluorescent chelate based assays for determining SAM, SAH and HCy provide series of advantages over assays that employ traditional organic fluorescent molecules.

The entire contents of the following provisional and non-provisional applications are incorporated by reference into the present non-provisional application as if they were denoted in their entirety:

U.S. Ser. No. 14/457,099 filed Aug. 11, 2014;
U.S. Ser. No. 14/218,928 filed Mar. 18, 2014;
U.S. Provisional Patent Application No. 61/801,547 filed on Mar. 15, 2013; and
U.S. Provisional Patent Application No. 62/143,790 filed Apr. 6, 2015.

Although the foregoing description (Angres) contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed is:

1. A fluorescent material conjugated to anti-SAH antibodies, wherein said fluorescent material is a fluorescent lanthanide chelate and wherein said monoclonal anti-SAH antibodies are derived from an hybridoma having the designation from the China Center For Type Culture Collection (CCTCC) number C2014178.

2. The fluorescent material of claim 1, wherein said lanthanide is selected from the group consisting of europium and terbium.

* * * * *